(12) United States Patent
Becker et al.

(10) Patent No.: US 10,206,781 B2
(45) Date of Patent: Feb. 19, 2019

(54) MODULAR DEVICE FOR PREVENTING COMPRESSION AND INSTABILITY IN A SEGMENTAL DEFECT REPAIR SCAFFOLD

(71) Applicants: Matthew Becker, Stow, OH (US);
Ennio Tasciotti, Houston, TX (US);
Bradley Weiner, Houston, TX (US);
Avraam Isayev, Fairlawn, OH (US)

(72) Inventors: Matthew Becker, Stow, OH (US);
Ennio Tasciotti, Houston, TX (US);
Bradley Weiner, Houston, TX (US);
Avraam Isayev, Fairlawn, OH (US)

(73) Assignees: The University of Akron, Akron, OH (US); Houston Methodist Hospital, Houston, TX (US)

( * ) Notice: Subject to any disclaimer, the term of this patent is extended or adjusted under 35 U.S.C. 154(b) by 0 days.

(21) Appl. No.: 15/310,981

(22) PCT Filed: May 13, 2015

(86) PCT No.: PCT/US2015/030530
§ 371 (c)(1),
(2) Date: Nov. 14, 2016

(87) PCT Pub. No.: WO2015/175637
PCT Pub. Date: Nov. 19, 2015

(65) Prior Publication Data
US 2017/0086978 A1    Mar. 30, 2017

Related U.S. Application Data

(60) Provisional application No. 61/992,318, filed on May 13, 2014.

(51) Int. Cl.
*A61F 2/28*     (2006.01)
*A61L 27/18*    (2006.01)
(Continued)

(52) U.S. Cl.
CPC ............ *A61F 2/2846* (2013.01); *A61L 27/18* (2013.01); *A61L 27/24* (2013.01); *A61L 27/3604* (2013.01);
(Continued)

(58) Field of Classification Search
CPC ...... A61F 2002/2835; A61F 2002/2839; A61F 2002/2842; A61F 2/2846; A61F 2002/285;
(Continued)

(56) References Cited

U.S. PATENT DOCUMENTS 5,211,664 A * 5/1993 Tepic .................... A61F 2/2846
606/60
5,275,602 A * 1/1994 Shimizu ................. A61B 17/80
606/331

(Continued)

FOREIGN PATENT DOCUMENTS

CN           102389329 A       3/2012

OTHER PUBLICATIONS

Reichert, R. Tissue Engineering Bone-Reconstruction of Critical Sized Segmental Bone Defects in a Large Animal Model, 2010, PhD thesis, Queensland University of Technology.
(Continued)

*Primary Examiner* — Alvin Stewart
(74) *Attorney, Agent, or Firm* — Renner Kenner Greive Bobak Taylor & Weber

(57) ABSTRACT

The present invention relates to a polymer scaffold design and method for treating segmental long bone defects without amputation that permits permanent regrowth of bone in the area of the segmental defect, without external fixation or other problems inherent in current systems. The polymer scaffold is preferably made from a poly(ester urea) polymer and includes an outer shell, sized to fit over a segmental
(Continued)

defect in a bone, and a collagen containing material. In some embodiments, the collagen containing material is placed in a polymer insert sized to fit within the segmental bone defect and within said outer shell. In some embodiments, the outer shell may contain struts running longitudinal struts along the inside surface of the outer shell. In some of these embodiments, the insert will have a corresponding set of grooves sized to receive the struts.

20 Claims, 7 Drawing Sheets

(51) Int. Cl.
  *A61L 27/24*   (2006.01)
  *A61L 27/36*   (2006.01)
  *A61L 27/58*   (2006.01)
  *A61F 2/30*   (2006.01)

(52) U.S. Cl.
  CPC .......... *A61L 27/3683* (2013.01); *A61L 27/58* (2013.01); *A61F 2002/30235* (2013.01); *A61L 2430/02* (2013.01)

(58) Field of Classification Search
  CPC ...... A61F 2002/2867; A61F 2002/2892; A61F 2002/30112; A61F 2002/30115; A61F 2002/30286; A61F 2002/30293; A61F 2002/30354; A61F 2002/30355; A61B 17/82; A61B 17/8855; A61B 17/842; A61L 27/3804; A61L 27/52; A61L 27/56
  See application file for complete search history.

(56) References Cited

U.S. PATENT DOCUMENTS

| | | | |
|---|---|---|---|
| 5,281,226 A * | 1/1994 | Davydov | A61B 17/72 606/63 |
| 5,660,225 A * | 8/1997 | Saffran | A61B 17/80 128/898 |
| 5,676,699 A * | 10/1997 | Gogolewski | C08L 89/00 623/16.11 |
| 6,077,076 A * | 6/2000 | Comfort | A61C 8/0006 433/173 |
| 6,214,049 B1 * | 4/2001 | Gayer | A61C 8/0006 623/16.11 |
| 6,312,467 B1 * | 11/2001 | McGee | A61F 2/28 623/16.11 |
| 6,719,793 B2 * | 4/2004 | McGee | A61F 2/28 623/16.11 |
| 6,827,743 B2 * | 12/2004 | Eisermann | A61B 17/68 623/23.54 |
| 7,131,995 B2 * | 11/2006 | Biedermann | A61F 2/2846 623/23.46 |
| 7,208,015 B2 * | 4/2007 | Pointillart | A61F 2/2846 623/23.51 |
| 7,753,963 B2 | 7/2010 | Boyer, II et al. | |
| 8,007,498 B2 * | 8/2011 | Mische | A61B 17/7258 606/100 |
| 8,197,520 B2 * | 6/2012 | Salemi | A61B 17/8085 606/280 |
| 8,546,456 B2 * | 10/2013 | Rose | A61B 17/72 521/88 |
| 8,669,107 B2 | 3/2014 | Detamore et al. | |
| 8,840,614 B2 * | 9/2014 | Mikhail | A61F 2/2803 606/86 R |
| 8,906,074 B2 * | 12/2014 | Kang | A61B 17/8076 606/283 |
| 9,060,823 B2 * | 6/2015 | Rose | A61L 27/56 |
| 9,452,049 B2 * | 9/2016 | Guldberg | A61L 27/3804 |
| 9,585,755 B2 * | 3/2017 | Rose | A61L 27/56 |
| 9,730,740 B2 * | 8/2017 | Rains | A61B 17/72 |
| 9,744,041 B2 * | 8/2017 | Henderson | A61L 27/16 |
| 9,782,259 B2 * | 10/2017 | Mikhail | A61F 2/2803 |
| 9,814,578 B1 * | 11/2017 | Gotfried | A61B 17/8095 |
| 2002/0032444 A1 * | 3/2002 | Mische | A61B 17/7258 606/63 |
| 2008/0208358 A1 * | 8/2008 | Bellamkonda | A61L 27/16 623/23.72 |
| 2008/0255560 A1 | 10/2008 | Myers et al. | |
| 2009/0036892 A1 | 2/2009 | Karidis et al. | |
| 2009/0180965 A1 | 7/2009 | Freyman et al. | |
| 2010/0168771 A1 * | 7/2010 | Guldberg | A61L 27/3804 606/151 |
| 2011/0029026 A1 * | 2/2011 | Nicolella | A61F 2/28 606/86 R |
| 2012/0029102 A1 * | 2/2012 | Rose | A61B 17/72 521/88 |
| 2013/0138155 A1 * | 5/2013 | Hoornaert | A61L 31/146 606/283 |
| 2013/0211540 A1 * | 8/2013 | Tate | A61B 17/56 623/23.57 |
| 2014/0039499 A1 * | 2/2014 | Rose | A61L 27/56 606/74 |
| 2014/0046454 A1 * | 2/2014 | Rose | A61B 17/72 623/23.58 |
| 2015/0173797 A1 * | 6/2015 | Ametani | A61F 2/2846 606/60 |
| 2015/0298068 A1 * | 10/2015 | Park | B01D 39/12 210/435 |
| 2015/0320463 A1 * | 11/2015 | Karmon | A61F 2/2846 606/74 |
| 2015/0366669 A1 * | 12/2015 | Bartee | A61L 27/18 623/23.5 |
| 2016/0106482 A1 * | 4/2016 | Rains | A61B 17/72 606/63 |
| 2016/0135955 A1 * | 5/2016 | Henderson | A61L 27/16 623/23.61 |
| 2016/0287390 A1 * | 10/2016 | Larsen | A61F 2/2846 |
| 2016/0287391 A1 * | 10/2016 | Larsen | A61F 2/2846 |
| 2017/0049477 A1 * | 2/2017 | Yeh | A61B 17/68 |
| 2017/0231767 A1 * | 8/2017 | Larsen | A61F 2/2846 623/23.58 |
| 2017/0312082 A1 * | 11/2017 | Henderson | A61L 27/16 |
| 2017/0340444 A1 * | 11/2017 | Mikhail | A61F 2/2803 |

OTHER PUBLICATIONS

Xie, S. Characterization and Fabrication of Scaffold Materials for Tissue Engineering—A thesis. May 2013, The Graduate Faculty of The University of Akron.

Wong, T. et al. Clinical Study: Masquelet Technique for Treatment of Posttraumatic Bone Defects. Feb. 6, 2014, The Scientific World Journal, vol. 2014, Article ID 710302.

* cited by examiner

MODULAR DEVICE FOR PREVENTING COMPRESSION AND INSTABILITY IN A SEGMENTAL DEFECT REPAIR SCAFFOLD

CROSS REFERENCE TO RELATED APPLICATIONS

This application claims the benefit of International Patent Application No. PCT/US2015/30530 entitled "Modular Device for Preventing Compression and Instability in a Segmental Defect Repair Scaffold" filed May 13, 2015, and U.S. provisional patent application Ser. No. 61/992,318 entitled "Modular Device for Preventing Compression and Instability In a Segmental Defect Repair Scaffold," filed May 13, 2014, both of which are incorporated herein by reference in their entirety.

REFERENCE TO GOVERNMENT SUPPORT

This invention was made with government support under grant number W911NF-09-1-004 awarded by Defense Advanced Research Projects Agency (DARPA). The government has certain rights in the invention.

FIELD OF THE INVENTION

One or more embodiments of the present invention relates to scaffolds and methods of treating segmental bone defects. In certain embodiments, the present invention relates to a modular scaffold and related methods of preventing compression and instability of segmental bone defects to facilitate repair and bone regrowth.

BACKGROUND OF THE INVENTION

Long bone defects represent a significant problem in orthopedic surgery. Current treatment strategies are often fraught with morbidity and complications for the patient and ample opportunity exists to improve current options. While a defect impairing the ability to bear load can occur in any long bone, the most common location is the tibial shall after trauma. The first treatment decision is whether limb salvage or primary amputation is best for the patient. Primary amputation is considered whenever a segmental long bone defect exceeds 10-30 cm. While primary amputation has several clinical advantages, the patient is permanently disabled and at increased risk for becoming destitute, divorced, or depressed. Limb salvage is possible in many circumstances and techniques often employed include limb shortening, distraction osteogenesis, autologous bone graft, free vascularized bone graft, and synthetic bone graft substitutes, all of which involve significant challenges, such as high rates of infection delayed union non-union, and—in major limb trauma—amputation. Patient morbidity, partial functional recovery, and poor quality of healing have long term impact on quality of life after injury. Rehabilitation is slow, painful, and the costs (emotionally, physically, and economically) are prohibitive. These challenges call attention to the significant need for innovation in the development of new bioactive materials and scaffold design.

What is needed in the art are anew method, bioactive material, and/or scaffold design for treating segmental long bone defects without amputation that permits permanent regrowth of bone in the area of the segmental defect, without the problems inherent in current systems.

SUMMARY OF THE INVENTION

In one or more embodiments, the present invention is directed to a polymer scaffold design and method for treating segmental long bone defects without amputation that permits permanent regrowth of bone in the area of the segmental defect, without external fixation or other problems inherent in current systems.

In a first aspect, the present invention is directed to a polymer scaffold for preventing compression and instability in a segmental bone defect comprising: an outer shell sized to fit over a segmental defect in a bone; said outer shell having a first end distal to said segmental defect, a second end proximal to said segmental defect; an inner surface, an outer surface, a thickness and an internal diameter; said inner surface defining an inner cavity; and a collagen containing material located within the inner cavity of said outer shell. In some embodiments, of this aspect of the present invention, the outer shell has one or more struts running along the inner surface of said outer shell between the first end and second end of said outer shell. In one or more embodiments, the polymer scaffold of the present invention includes any one or more of the above referenced embodiments of the first aspect of the present invention, further comprising an insert sized to fit within said segmental bone defect and within said outer shell; said insert having a lower distal end, an upper proximal end, an inner surface, an outer surface, and a central cavity; wherein said collagen containing material is located within the central cavity of said insert.

In one or more embodiments, the polymer scaffold of the present invention includes any one or more of the above referenced embodiments of the first aspect of the present invention, wherein: said outer shell has one or more struts running along the inner surface of said outer shell between the first end and second end of said outer shell; and said insert has one or more grooves running along the outer surface of said surface substantially hollow insert; said one or more grooves sized to receive the one or more struts running along the inner surface of said outer shell. In one or more embodiments, the polymer scaffold of the present invention includes any one or more of the above referenced embodiments of the first aspect of the present invention, wherein said outer shell comprises a degradable poly(urethane), poly(ester urea), poly(carbonate) or poly(ester) polymer.

In one or more embodiments, the polymer scaffold of the present invention includes any one or more of the above referenced embodiments of the first aspect of the present invention, wherein said outer shell comprises poly(bis-L-phenylalanine-1,6-hexane-diester urea) (poly(1-PHE-6)), poly(bis-L-phenylalanine-1,8-octane-diester urea) (poly(1-PHE-8)), poly(bis-L-phenylalanine-1,10-decane-diester urea) (poly(1-PHE-10)), poly(bis-L-phenylalanine-1,12-dodecane-diester urea) (poly(1-PHE-12)), poly(bis-L-phenylalanine-1,14-tetradecane-diester urea) (poly(1-PHE-14)), poly(bis-L-phenylalanine-1,16-hexadecane-diester urea) (poly(1-PHE-16)), poly(bis-L-phenylalanine-1,18-octadecane-diester urea) (poly(1-PHE-18)), poly(bis-L-phenylalanine-1,20-isosane-diester urea) (poly(1-PHE-20)), poly(bis-4-I-L-phenylalanine-1,6-hexanediol-diester urea) (poly(1-IPHE-6)), poly(bis-4-I-L-phenylalanine-1,8-octanediol-diester urea) (poly(1-IPHE-8)), poly(bis-4-I-L-phenylalanine-1,10-decanediol-diester urea) (poly(1-IPHE-10)), poly(bis-4-I-L-phenylalanine-1,12-dodecanediol-diester urea) (poly(1-IPHE-12)), poly(bis-4-I-L-phenylalanine-1,14-tetradecanediol-diester urea) (poly(1-IPHE-14)), poly(bis-4-I-L-phenylalanine-1,16-hexadecanediol-diester urea) (poly(1-IPHE-16)), poly(bis-4-I-L-phenylalanine-1,18-octadecanediol-diester urea) (poly(1-IPHE-18)), poly(bis-4-I-L-phenylalanine-1,20- isosanediol-diester urea) (poly(1-IPHE-20)), poly(bis-L-phellylalanine-hexane-1,6-diester-co-tri-O-benzyl-L-tyrosine-1,1,1-trimethyl ethane-triester urea), or combinations and/or copolymers thereof. In one or more embodiments, the polymer scaffold of the present invention includes any one or more of the above referenced embodiments of the first aspect of the present invention, wherein said outer shell is radiopaque.

In one or more embodiments, the polymer scaffold of the present invention includes any one or more of the above referenced embodiments of the first aspect of the present invention, wherein the internal diameter of said outer shell is from about 1 cm to about 5 cm. In one or more embodiments, the polymer scaffold of the present invention includes any one or more of the above referenced embodiments of the first aspect of the present invention, wherein the thickness of said outer shell is from about 2 mm to about 6 cm. In one or more embodiments, the polymer scaffold of the present invention includes any one or more of the above referenced embodiments of the first aspect of the present invention, wherein the inner surface of said outer shell has from about 2 to about 5 struts. In one or more embodiments, the polymer scaffold of the present invention includes any one or more of the above referenced embodiments of the first aspect of the present invention, wherein the struts comprise from about 2% to about 20% of the internal diameter of said outer shell.

In one or more embodiments, the polymer scaffold of the present invention includes any one or more of the above referenced embodiments of the first aspect of the present invention, wherein said struts have a rounded cross sectional shape. In one or more embodiments, the polymer scaffold of the present invention includes any one or more of the above referenced embodiments of the first aspect of the present invention, wherein said struts are symmetrically oriented around the inner surface of said outer shell. In one or more embodiments, the polymer scaffold of the present invention includes any one or more of the above referenced embodiments of the first aspect of the present invention, wherein the grooves running along the outer surface of said surface substantially hollow insert have a triangular, rectangular, square or rounded cross sectional shape. In one or more embodiments, the polymer scaffold of the present invention includes any one or more of the above referenced embodiments of the first aspect of the present invention, wherein said collagen containing material comprises decellularized horse tendon.

In a second aspect, the present invention is directed to a method of treating a segmental bone defect using a polymer scaffold comprising: applying anesthesia to the patient; surgically exposing the segmental bone defect, if not already exposed; determining whether the segmental bone defect is continuous or not continuous; if the bone at the segmental bone defect is not continuous, identifying a first bone end above said segmental bone defect and a second bone end below said segmental bone defect; if the bone at the segmental bone defect is continuous, cutting through the bone at the segmental bone defect to create said first bone end and said second bone end; preparing a polymer scaffold comprising an outer shell and a collagen containing material; said outer shell having a first end sized to fit over said first bone end, a second end sized to fit over said second bone end, an inner cavity, and a length that is greater than the length of said segmental bone defect; placing the collagen containing material in the inner cavity of said outer shell; sliding the first end of said polymer shell over said first bone end and securing it in place with a non-toxic adhesive; sliding the second end of said polymer scaffold over said second bone end and securing it in place with a non-toxic adhesive; surgically closing the wound exposing said segmental bone defect.

In some embodiments, the method further comprises: preparing a polymer insert sized to fit inside said outer shell and between said first bone end and said second bone end, said polymer insert having a first end, a second end, an inner surface, an outer surface, and a central cavity; placing a collagen containing material within the central cavity of said polymer insert; and placing said polymer insert in the inner cavity of said outer shell. In one or more embodiments, the method for treating a segmental bone defect using a polymer scaffold of the present invention includes any one or more of the above referenced embodiments of the second aspect of the present invention, wherein: said outer shell has one or more struts running along the inner surface of said outer shell between the first end and second end of said outer shell; and said polymer insert has one or more grooves running along the outer surface of said surface substantially hollow insert; said one or more grooves sized to receive the one or more struts running along the inner surface of said outer shell.

BRIEF DESCRIPTION OF THE DRAWINGS

For a more complete understanding of the features and advantages of the present invention, reference is now made to the detailed description of the invention along with the accompanying figures in which:

FIG. 3A shows that the in vitro degradation time of Poly(1-PHE-6) is minimal out to 16 weeks (<1% by mass).

FIG. 3B shows that the PEU polymers made with longer diols exhibited faster degradation (~5%).

FIG. 9A is an image taken from a slide of a Masson's Trichrome staining showing a saggital section of the sheep regenerating long-bone defect after 4 weeks post implant showing the periosteum (P), newly forming bone (NB); outer shell (S), and bone marrow (BM). FIG. 9B is an enlargement of the image of FIG. 9A showing adherence of native periosteum to either the cortical portion of the tibia or the outer shell associated with a significant cellular activity/proliferation and novel bone formation with early endochondral ossification. FIG. 9C is an enlargement of the image of FIG. 9A showing details of the endochondral ossification in the newly forming bone (NB) in comparison to the native tissue (FIG. 9D). FIG. 9E is an enlargement of the image of FIG. 9A showing areas of fusion at the interface of native tibia (T), PEU outer shell (S) and novel bone (white arrow).

DETAILED DESCRIPTION OF THE ILLUSTRATIVE EMBODIMENTS

The present invention is directed to a polymer scaffold design and method for treating segmental long bone defects without amputation that permits permanent regrowth of bone in the area of the segmental defect, without external fixation or other problems inherent in current systems. As used herein, a segmental detect in a bone refers to an orthotopic defect that will not heal without intervention. By classical definition, a critical size defect is the smallest size tissue defect that will not completely heal over the natural lifetime of a patient. Materials or strategies that cause complete regeneration of the bone in these defects are considered to bridge nonunion defects, or are capable of generating bone at a site and time when bone would otherwise not be present.

Figure 1:
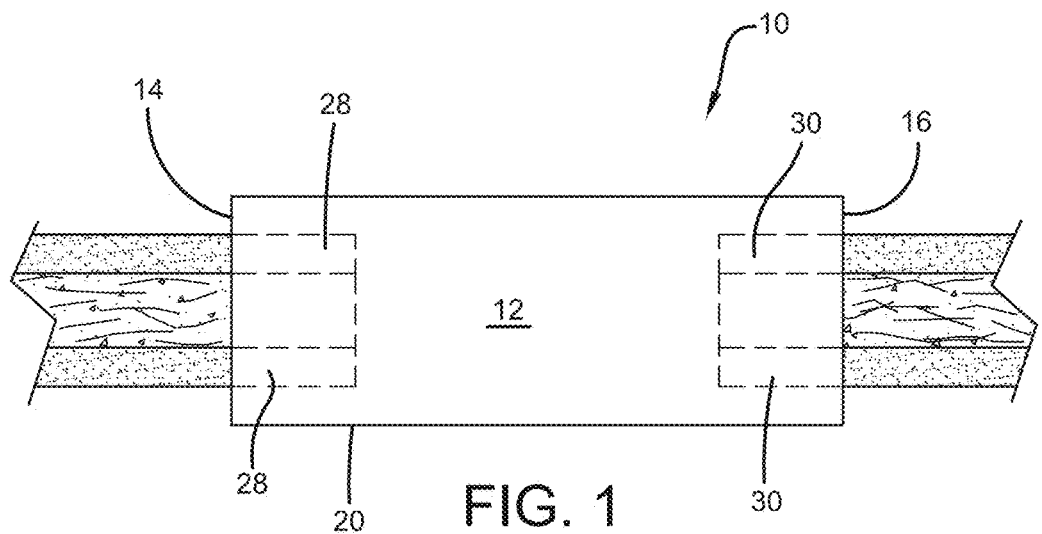
FIG. 1 is a front view of a polymer scaffold for preventing compression and instability in a segmental bone defect according to one or more embodiments of the present invention.
Figure 2A:
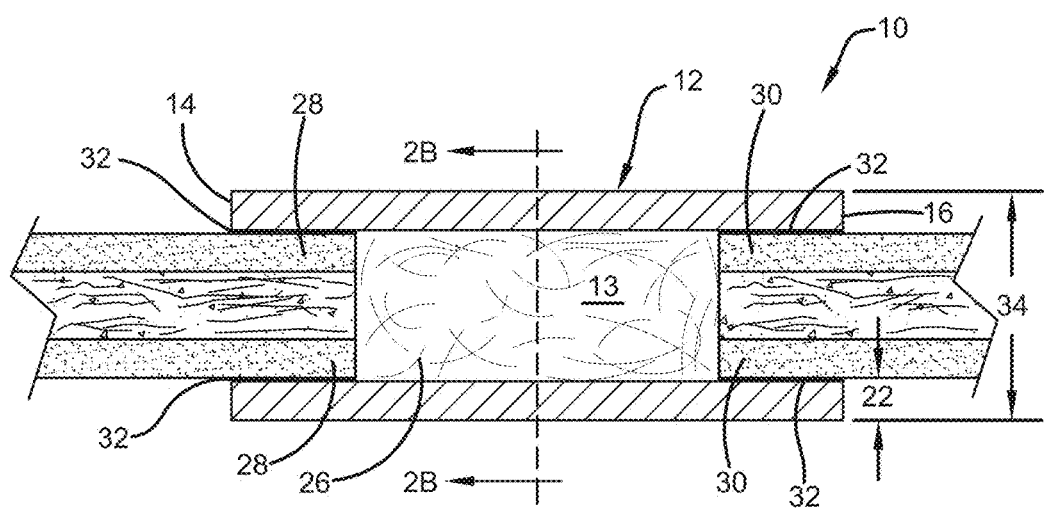
FIG. 2A is a cross sectional view of the polymer scaffold for preventing compression and instability in a segmental bone defect shown in FIG. 1 taken along the bone axis.
Figure 2B:
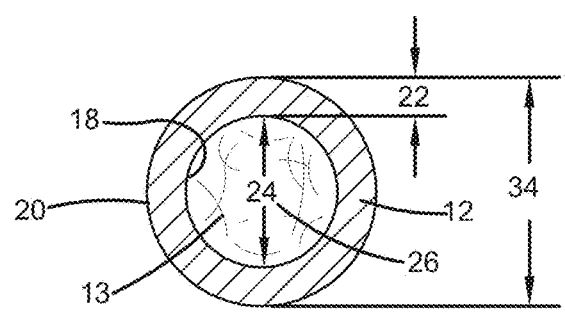
FIG. 2B is a cross sectional view of a polymer scaffold for preventing compression and instability in a segmental bone defect shown in FIG. 1 taken transverse to the bone axis as shown in FIG. 2A.

Referring now to FIGS. 1 and 2A-B, a polymer scaffold for preventing compression and instability in a segmental bone defect is shown, generally indicated by the numeral 10. Polymer scaffold 10 includes an outer shell 12 sized to fit over a segmental defect in a bone, and a collagen containing material 13. Outer shell 12 has a first end 14 proximal to the segmental defect, a second end 16 distal to said segmental defect, an inner surface 18, an outer surface 20, a thickness 22 and an internal diameter 24. The inner surface 18 of outer shell 12 defines an inner cavity 26 in which a collagen containing material 13, such as decellularized horse tendon, may be placed to facilitate bone regrowth. In the embodiment shown in FIGS. 2A and 2B, outer shell 12 may be a straight or tapered hollow tube sized to span the length of a segmental defect and fit over the bone ends above 28 and below 30 the segmental defect.

Outer shell 12 may be secured to bone ends 28, 30 by any means known in the art including non-toxic adhesives or mechanical fasteners. In some embodiments, outer shell 12 is secured to the bone end 28, 30 with a suitable non-toxic adhesive 32 (See FIG. 2A). Suitable non-toxic adhesives 32 include, without limitation, non-toxic epoxy and methyl methacrylate adhesives. In some embodiments, the outer shell 12 is secured to the bone with Poly Methyl Methacrylate (PMMA) or other similar crosslinkable polymer adhesives 32. Adhesive 32 should provide a bond strong enough to prevent both linear and rotational movement of the outer shell 12 and bone ends 28, 30 with respect each other during weight bearing activities after surgery.

As will be appreciated by those of skill in the art, the appropriate inner diameter 24 of outer shell 12 will depend upon the diameter of the bone upon which it is to be used. As should be apparent, inner diameter 24 of outer shell 12 must be large enough to fit over bone ends 28, 30 at either end of the defect, but small enough to permit the adhesive 32 to properly bond outer shell 12 to bone ends 28,30. Further, the outer shell 12 should not fit so tightly over the bone ends 28, 30 that there is insufficient room for enough adhesive 32 to create sufficient binding force. In some embodiments, inner diameter 24 of outer shell 12 is from about 0.2 cm to about 5 cm. In some embodiments, inner diameter 24 of outer shell 12 is from about 1 cm to about 5 cm. In some embodiments, inner diameter 24 of outer shell 12 is from about 1 cm to about 2 cm.

It is expected, moreover, that the outer shell 12 overlap the bone ends 28, 30 to provide sufficient surface area for the adhesive 32 to create a sufficient binding force to prevent movement of the outer shell 12 relative to bone ends 28, 30. The amount of overlap required will, of course, depend upon such things as the specific bone involved, the fit of the outer shell 12 over the bone ends 28, 30, and the type of adhesive used. Ideally, there should be enough overlap to ensure proper adhesive force, but not so much overlap as to unnecessarily interfere with the surrounding tissues. In some embodiments, there is from about 1.0 to about 1.5 cm overlap of the outer shell 12 and the bone ends 28, 30.

Outer shell 12 may have any length, but should be long enough to cover the defect and overlap bone ends 28, 30 as set forth above. In some embodiments, outer shell 12 is from about 0.5 cm to about 100 cm in length. In some embodiments, outer shell 12 is from about 1 cm to about 50 cm in length. In some embodiments, outer shell 12 is from about 2 cm to about 20 cm in length. In some embodiments, outer shell 12 is from about 2 cm to about 10 cm in length.

Depending upon the bone involved and the location of the defect on the bone, the width of the bone at the upper and lower bone ends 28, 30 may be different. In these embodiments, outer shell 12 may be tapered, having a larger inner diameter 24 at one end than at the other end to account for the corresponding differences in width of the bone at bone ends 28, 30. In some other embodiments, outer shell 12 is a straight tube (has a consistent inner and outer diameter) and any gap between the inner surface 18 of the outer shell 12 and the outer surface of the bone end may be shimmed using pieces of the polymer material used to form the outer shell 12 and secured using adhesive 32, as set forth above.

Outer shell 12 further has a thickness 22 defined by its outer diameter 34 and its inner diameter 24. As will be apparent to those of skill in the art, the proper thickness 22 of outer shell 12 will depend upon various factors including the bone involved, the size and length of the defect, the location of the defect, whether the bone is weight bearing, the weight or other force to be applied, and the material used to form outer shell 12. Outer shell 12 should have sufficient thickness 22 to provide the mechanical strength necessary to support a patient's weight or whatever forces are to be applied across the segmental defect during treatment and recovery, without being so thick as to unnecessarily interfere with the surrounding tissues and should allow a natural, grafted, or artificial periosteum to be secured circumferentially around the repair site. In some embodiments, a natural, grafted, or artificial periosteum may be secured circumferentially around the repair sight with a suture. One of ordinary skill in the art will be able to determine a proper thickness 22 for the outer shell 12 without undue experimentation. In some embodiments, outer shell 12 has a thickness 22 of from about 0.1 mcm to about 6 cm. In some embodiments, outer shell 12 has a thickness 22 of from about 0.1 cm to about 3.0 cm. In some embodiments, outer shell 12 has a thickness 22 of from about 0.1 cm to about 2.0 cm. In some embodiments, outer shell 12 has a thickness 22 of from about 0.2 cm to about 1.5 cm.

Outer shell 12 may be composed of any non-toxic polymer having the mechanical strength necessary to support the patient's weight or whatever forces are to be applied across the segmental defect during treatment and recovery. Outer shell 12 is preferably, but need not be, made from a degradable polymer. In some embodiments, outer shell 12 comprises a degradable poly(urethane), poly(ester urea), poly(ester) or poly(carbonate) polymer having the required mechanical properties.

In some embodiments, outer shell 12 comprises a linear or branched amino acid based poly(ester urea) (PEU) polymer and, in particular, may comprise one or more L-phenylalanine-based poly(ester urea)s (PEU). Polymers created with monomeric units that are comprised of biomimetic and simple structures, such as amino acids and simple polyols, are generally associated with minimal risks for biocompatibility and in vivo immunostimulatory side effects. Moreover, unlike generally available degradable polyesters, such as poly(L-lactic acid) (PLLA), PEUs does not lead to local acidosis and inflammation during degradation because the byproducts are buffered by urea linkages at each monomeric subunit. In some embodiments, suitable PEU polymers are obtained through a step growth polymerization process and have reported molecular mass distributions are narrower that the theoretical values due to the fractionation that occurs during precipitation. In some embodiments, suitable PEU polymers are obtained through interfacial polycondensation polymerization reactions of monomers made by reacting amino acids with linear or branched hydroxyl functionalized polyols.

The PEU polymers used to fabricate the present invention may be synthesized using any of the various methods known in the art for forming PEU polymers. In some embodiments, these PEU polymers may be synthesized as shown in Scheme 1 below.

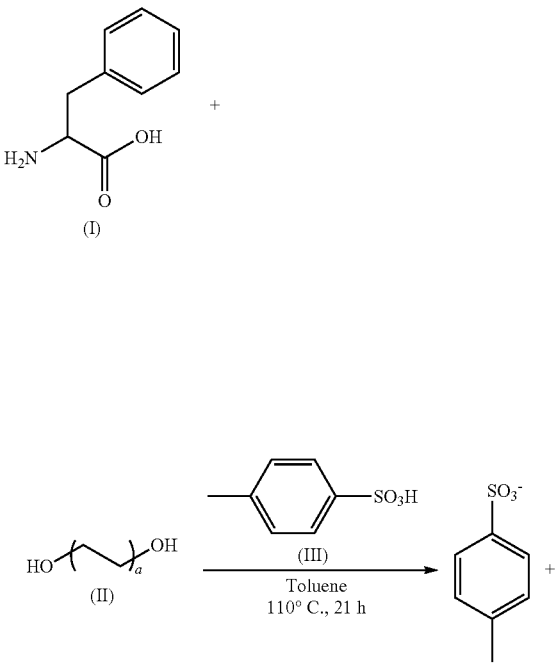

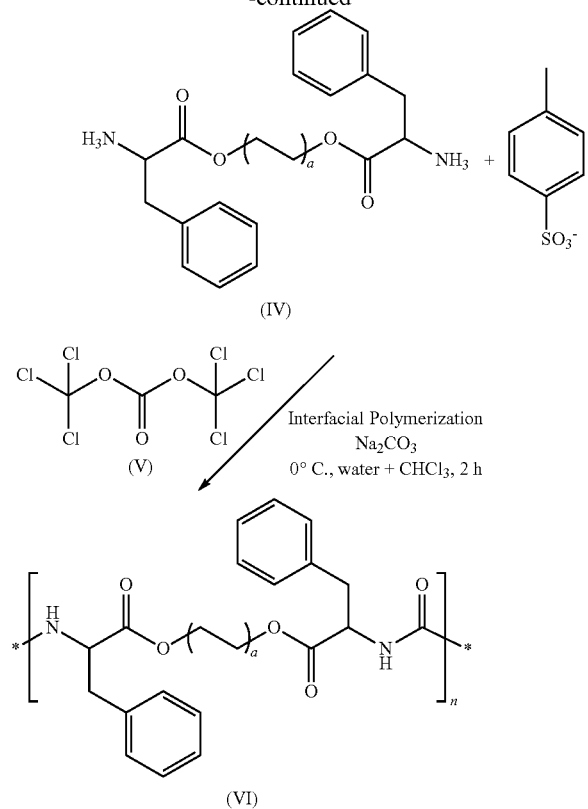

(IV)

(V)

(VI)

wherein a is an integer from about 1 to about 10, and n is an integer from about 10 to about 1000. The amino acid starting material (I) shown in Scheme 1 is L-phenylalanine, but is should be appreciated that the present invention is not to be so limited. In various embodiments of the present invention, the amino acid starting material (I) may be any functionalized or non-functionalized α-amino acid or combination of α-amino acids other than proline. In some embodiments, the starting material may be alanine (ala—A); arginine (arg—R); asparagine (asn—N); aspartic acid (asp—D); cysteine (cys—C); glutamine (gln—Q); glutamic acid (glu—E); glycine (gly—G); histidine (his—H); isoleucine (ile—I); leucine (leu—L); lysine (lys—K); methionine (met—M); phenylalanine (phe—F); serine (ser—S); threonine (thr—T); tryptophan (trp—W); tyrosine (tyr—Y); valine (val—V) or combinations thereof. In some of these embodiments, the amino acid starting material (I) may comprise L-phenylalanine, which is commercially available from Sigma Aldrich Company LLC (St. Louis, Mo.) or Alfa Aesar (Ward Hill, Mass.) and/or 4-iodo-L-phenylalanine, which is commercially available from VWR International LLC (Radnor, Pa.).

In these embodiments, the amino acid starting material (I) is then reacted with a linear or branched polyol (II) having from 2 to 60 carbon atoms to form an acid salt of the polyester monomer (IV) that will be used to form the PEU (VI), as shown in Scheme 1. In some embodiments, the polyol (II) has from 2 to 40 carbon atoms. In some embodiments, the polyol has from 2 to 20 carbon atoms. In some embodiments, the polyol has from 2 to 10 carbon atoms. In some embodiments, the polyol may be a diol, triol, or tetraol. The polyol shown in of Scheme 1, is a diol having from 2 to 20 carbon atoms. In some embodiments, the polyol is a diol having from 2 to 17 carbon atoms. In some embodiments, the polyol is a diol having from 2 to 13 carbon atoms. In some embodiments, the polyol is a diol having from 2 to 10 carbon atoms. In some embodiments, the polyol is a diol having from 10 to 20 carbon atoms. In some embodiments, the polyol is a diol having 3 carbon atoms.

Suitable polyols may include, without limitation, 1,6-hexanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, 2-butene-1,4-diol, 3,4-dihydroxy-1-butene, 7-octene-1,2-diol, 3-hexene-1,6-diol, 1,4-butynediol, trimethylolpropane allyl ether, 3-allyloxy-1,2-propanediol, 2,4-hexadiyne-1,6-diol, 2-hydroxymethyl-1,3-propanediol, 1,11-Tris(hydroxymethyl)propane, 1,1,1-tris(hydroxymethyl)ethane, pentaerythritol, di(trimethylolpropane) dipentaerythritol and combinations thereof. In the embodiments, the polyol may be 1,6-hexanediol and is commercially available from Sigma Aldrich Company LLC (St. Louis, Mo.) or Alfa Aesar (Ward Hill, Mass.).

The reaction of the amino acid (I) with the polyol (II) to create an amino acid functionalized monomer salt (IV) can be achieved in any number of ways generally known to those of skill in the art. Generally, a condensation reaction at temperatures exceeding the boiling point of water involving a slight molar excess (~2.1 eq.) of the amino acid relative to the hydoxy groups of the polyol is sufficient to enable the reaction to proceed. The presence of toluene sulphonic acid (III) or another proton source, is necessary to protonate the amine on the amino acid and ensure that trans amidation reactions do not occur at higher conversions.

Next, the amino acid based polyester monomer salt is reacted with a "PEU forming compound" to form a PEU. As used herein, the term "PEU forming compound" refers to a compound capable of placing a carboxyl group between two amine groups, thereby forming a urea bond and includes, without limitation, triphosgene (V), diphosgene, or phosgene. As will be appreciated by those of skill in the art, diphosgene (a liquid) and triphosgene (V) (a solid crystal) are understood to be more suitable than phosgene because they are generally appreciated as safer substitutes to phosgene, which is a toxic gas. The reaction of an amino acid functionalized monomer with triphosgene (V), diphosgene or phosgene to create an amino acid-based PEU can also be achieved in any number of ways generally known to those of skill in the art.

In some embodiments, the amino acid based polyester monomer salt (IV) is combined with a first fraction of a suitable base such as sodium carbonate, potassium carbonate, sodium bicarbonate, or potassium bicarbonate, and dissolved in water using mechanical stirring and a warm water bath (approximately 35° C.). The reaction is then cooled to a temperature of from about −10° C. to about 2° C. and an additional fraction of base is dissolved in water and added to the reaction mixture. Next, a first fraction of a PEU forming compound, such as triphosgene (V), is dissolved in a suitable solvent and added to the reaction mixture. One of ordinary skill will be able to select a suitable solvent for the PEU forming compound without undue experimentation. Selection of a suitable solvent for the PEU forming compound will, of course, depend upon the particular compound chosen, but may include, without limitation, distilled chloroform dichloromethane, or dioxane.

After a period of from about 2 to about 60 minutes, a second fraction of the PEU forming compound is dissolved in a suitable solvent, such as distilled chloroform or dichloromethane, and added dropwise to the reaction mixture over a period of from about 0.5 to about 12 hours to produce a crude PEU polymer. The crude product may be purified using any means known in the art for that purpose. In some embodiments, the crude homopolymer product may be purified by transferring it into a separatory funnel and precipitating it into boiling water.

While Scheme 1 shows the formation of a PEU homopolymer, the invention is not to be so limited. As will be appreciated by those of skill in the art, two or more different amino acid based polyester monomer salts (IV) may be prepared and reacted as set forth above to form copolymers. In some embodiments, suitable PEU polymers may be made as set forth in International Published Patent Application No. WO 2015/048728, the disclosure of which is hereby incorporated by reference in their entirety.

In some embodiments, these reactions produce yield high molecular mass materials (See Table 1, below) suitable for compression molding.

Suitable linear or branched amino acid based poly(ester urea) (PEU) polymers may include, without limitation poly (bis-L-phenylalanine-1,6-hexane-diester urea) (poly(1-PHE-6)), poly(bis-L-phenylalanine-1,8-octane-diester urea) (poly(1-PHE-8)), poly(bis-L-phenylalanine-1,10-decane-diester urea) (poly(1-PHE-10)), poly(bis-L-phenylalanine-1,12-dodecane-diester urea) (poly(1-PHE-12)), poly(bis-L-phenylalanine-1,14-tetradecane-diester urea) (poly(1-PHE-14)), poly(bis-L-phenylalanine-1,16-hexadecane-diester urea) (poly(1-PHE-16)), poly(bis-L-phenylalanine-1,18-octadecane-diester urea) (poly(1-PHE-18)), poly(bis-L-phenylalanine-1,20-isosane-diester urea) (poly(1-PHE-20)), poly(bis-4-I-L-phenylalanine-1,6-hexanediol-diester urea) (poly(1-IPHE-6)), poly(bis-4-I-L-phenylalanine-1,8-octanediol-diester urea) (poly(1-IPHE-8)), poly(bis-4-I-L-phenylalanine-1,10-decanediol-diester urea) (poly(1-IPHE-10)), poly(bis-4-I-L-phenylalanine-1,12-dodecanediol-diester urea) (poly(1-IPHE-12)), poly(bis-4-I-L-phenylalanine-1,14-tetradecanediol-diester urea) (poly(1-IPHE-14)), poly(bis-4-I-L-phenylalanine-1,16-hexadecanediol-diester urea) (poly(1-IPHE-16)), poly(bis-4-I-L-phenylalanine-1,18-octadecanediol-diester urea) (poly(1-IPHE-18)), poly(bis-4-I-L-phenylalanine-1,20-isosanediol-diester urea) (poly(1-IPHE-20)), poly(bis-L-phellylalanine-hexane-1,6-diester-co-tri-O-benzyl-L-tyrosine-1,1,1-trimethyl ethane-triester urea), or combinations and/or copolymers thereof.

In some embodiments, outer shell 12 may comprise one or more PEU polymers having the formula:

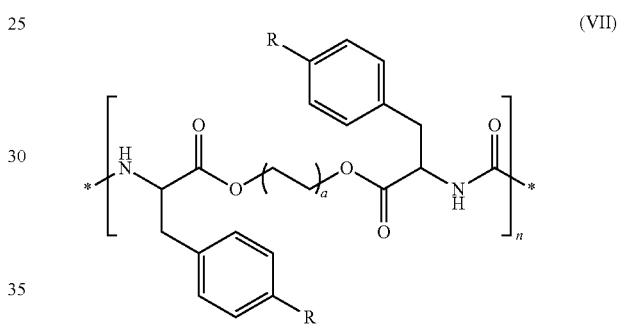

(VII)

TABLE 1

Characterization Data Summary for Poly(ester) and Poly(ester urea) Polymers

| POLYMER | $M_w$ | $M_w/M_n$ | $T_g$ | $T_m$ | $T_d$ | Young's Modulus (GPa) | Stiffness (N/m) | Flexural Stress (MPa) | Flexural Modulus (GPa) |
|---|---|---|---|---|---|---|---|---|---|
| PLLA | 64,000 | 1.82 | 55 | 175 | 392 | 1.2 ± 0.9 | 55.0 ± 0.9 | 29.0 ± 0.9 | 2.8 ± 0.9 |
| Poly(1PHE-6) | 84,000 | 2.42 | 77 | 153 | 335 | 3.1 ± 0.2 | 71.1 ± 5.1 | 36.9 ± 4.0 | 3.2 ± 0.5 | wherein R is H, OH, F, I, $OCH_2C\equiv CH$, $OCH_2CH_2CH_2N_3$, $OCH_2CH_2CH_2CH=CH_2$, $OCH_2Ph$, $OCOCH_2CH_2COCH_3$; a is an integer from 2 to 10; and n is an integer from about 10 to 1000. In some embodiments, outer shell 12 may comprise one or more PEU polymers having the formula:

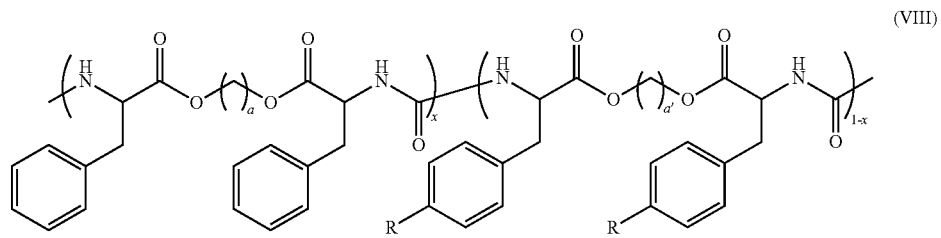

(VIII)

wherein R is an oxygen atom connected to a alkyl or aryl group containing an alkyne group, an alkene group, an azide group, a benzyl protected phenol group, a ketone group or a strained cyclooctyne; x is a mole fraction of from 0.001 to 0.200; and a and a' are integers from 2 to 10. In some of these embodiments, R may be OH, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$.

In one or more embodiments, the outer shell 12 may be made from one or more PEU polymers having a formula selected from:

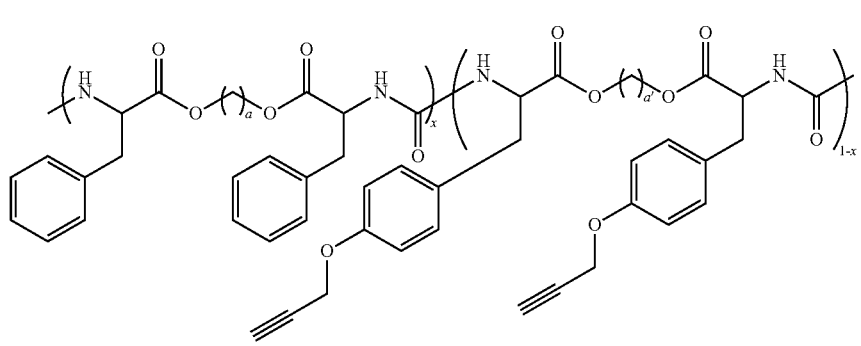

(IX)

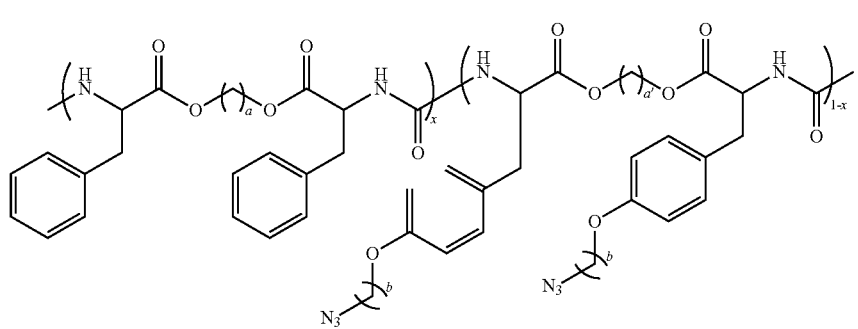

(X)

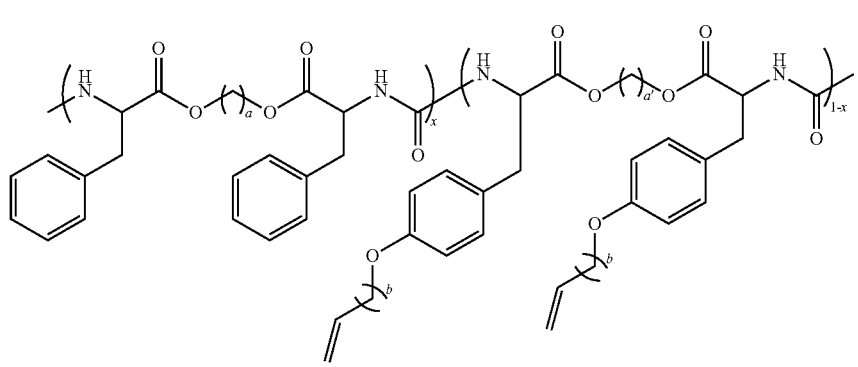

(XI)

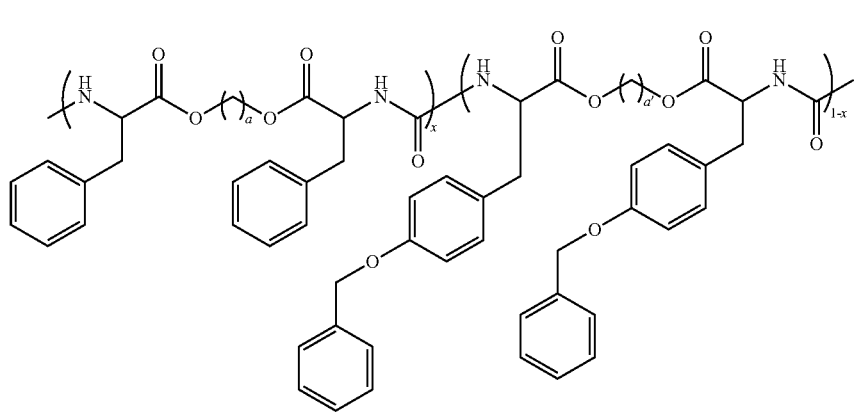

(XII)

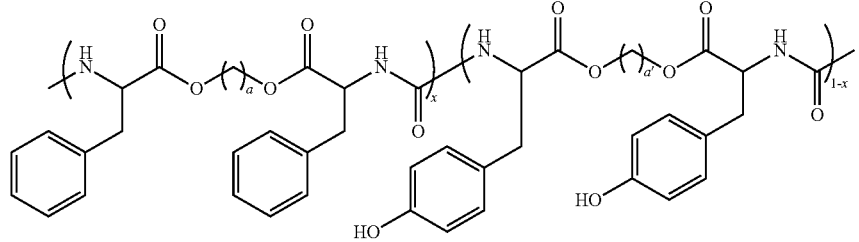

(XIII)

, and

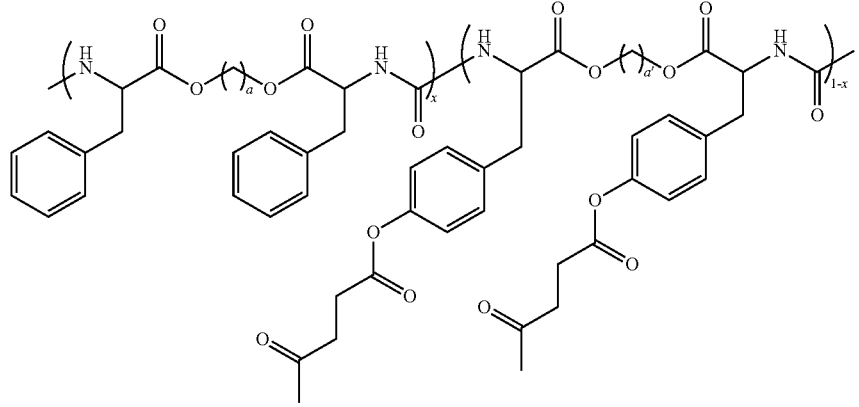

(XIV)

, wherein a and a' are each an integer from 2 to 12; b is an integer from 1 to 8; and x is a molar fraction from 0.001 to 0.200. In one or more embodiments, the amino acid based poly(ester urea) polymer of the present invention includes any one or more of the above referenced embodiments of the first aspect of the present invention having a mole average molecular weight of from about 30,000 da to about 300,000 da.

In some embodiments, the outer shell may comprise one or more phenylalanine (PHE) based PEU polymers formed using a 1,6-hexane diol (a=6) (poly(1-PHE-6)), and having the formula:

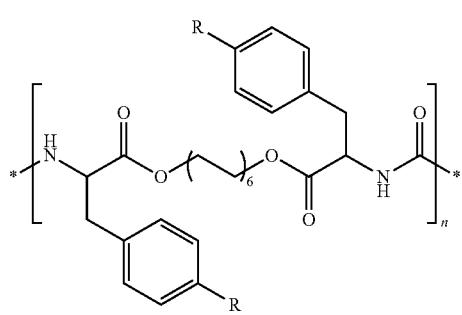

(XV)

wherein R is H; and n is an integer from about 10 to about 1000. In some embodiments, R is may also be OH, I, F, $OCH_2C\equiv CH$, $OCH_2CH_2CH_2N_3$, $OCH_2CH_2CH_2CH=CH_2$, $OCH_2Ph$, or $OCOCH_2CH_2COCH_3$.

As set forth above, while preferably degradable, outer shell 12 should have sufficient mechanical strength to permit weight bearing activities at least until there has been sufficient bone regrowth to permit weight bearing use of the bone without such support. Accordingly, these polymers should have both the necessary intrinsic mechanical properties to permit weight bearing activities and a degradation profile that maintains those properties at least until there has been sufficient bone regrowth to permit weight bearing use of the bone without such support. Thus, PEU polymers used to form outer shell 12 will generally have weight average molecular weights ($M_w$) of from about 30,000 to about 300,000. In some embodiments, the PEU polymers used to form outer shell 12 will have a $M_w$ of from about 30,000 to about 150,000. In some embodiments, the PEU polymers used to form outer shell 12 will have a $M_w$ of from about 30,000 to about 100,000. In some embodiments, the PEU polymers used to form outer shell 12 will have a $M_w$ of from about 50,000 to about 100,000. In some embodiments, the PEU polymers used to form outer shell 12 will have a $M_w$ of from about 75,000 to about 100,000.

Figure 3A:
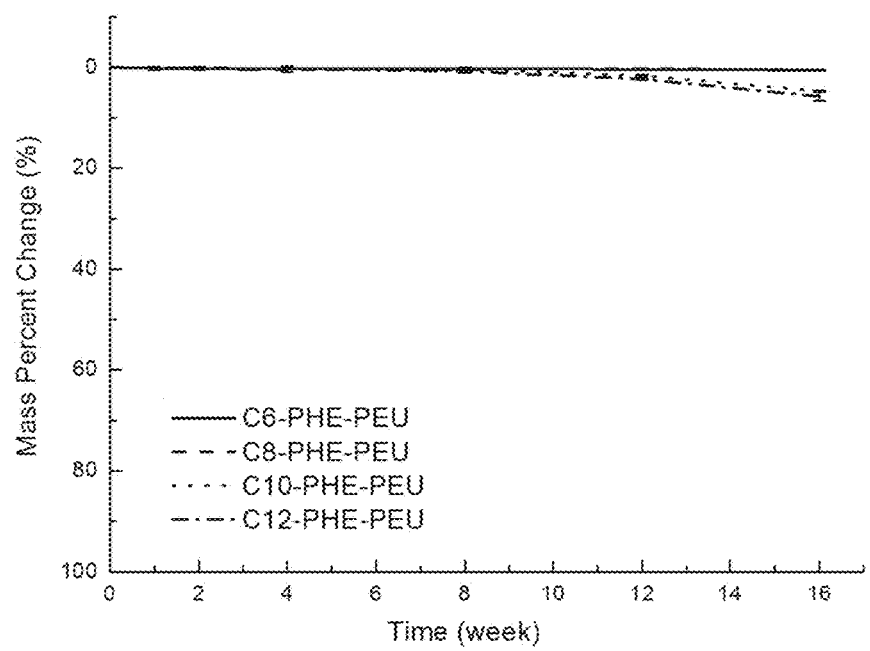
FIG. 3A is a graph showing the in vitro degradation over time of phenylalanine based PEU polymers prepared with different length diols.
Figure 3B:
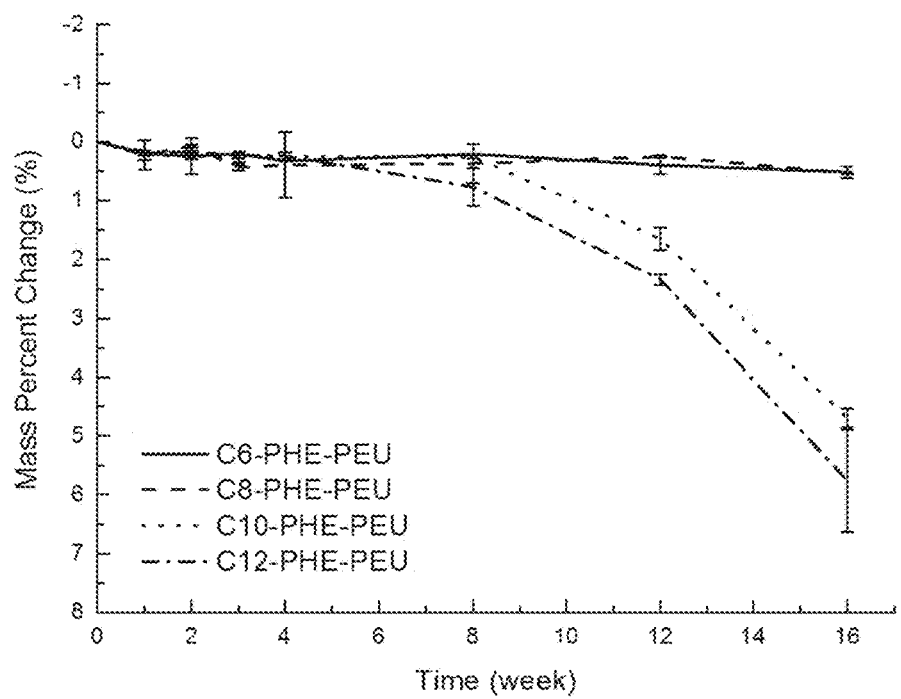
FIG. 3B is a graph showing the in vitro degradation over time of phenylalanine based PEU polymers prepared with different length diols.
Figure 4A:
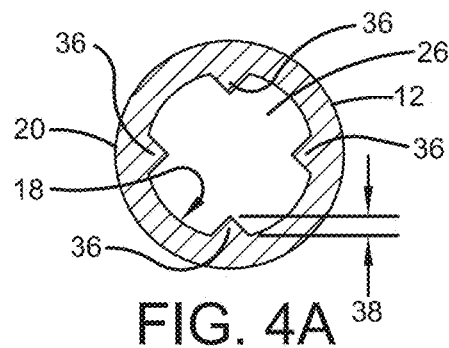
FIG. 4A is a cross sectional view of a polymer scaffold for preventing compression and instability in a segmental bone defect according to one or more embodiments of the present invention taken transverse the bone axis showing four triangular struts.
Figure 4C:
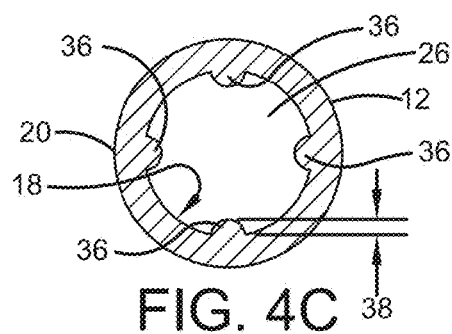
FIG. 4C is a cross sectional view of a polymer scaffold for preventing compression and instability in a segmental bone defect according to one or more embodiments of the present invention taken transverse the bone axis showing four rounded struts.
Figure 4D:
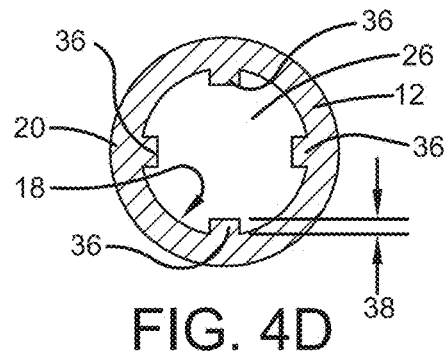
FIG. 4D is a cross sectional view of a polymer scaffold for preventing compression and instability in a segmental bone defect according to one or more embodiments of the present invention taken transverse the bone axis showing four rectangular struts.
Figure 4B:
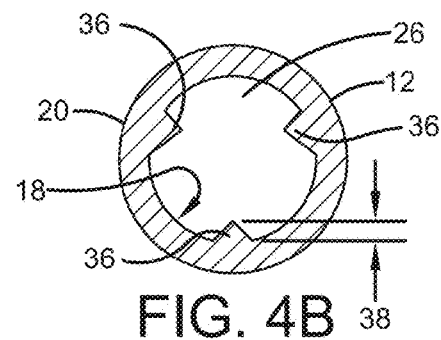
FIG. 4B is a cross sectional view of a polymer scaffold for preventing compression and instability in a segmental bone defect according to one or more embodiments of the present invention taken transverse the bone axis showing three triangular struts.
Figure 5A:
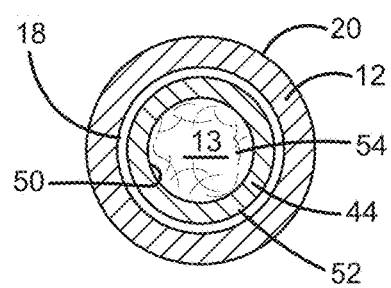
FIG. 5A is a cross sectional view of a polymer scaffold for preventing compression and instability in a segmental bone defect according to one or more embodiments of the present invention taken transverse the bone axis showing the spacial relationship between the struts on the outer shell and grooves in the substantially hollow insert.
Figure 5B:
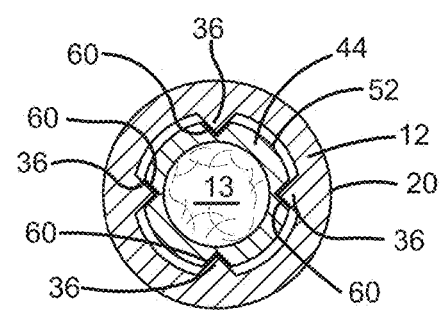
FIG. 5B is a cross sectional view of a polymer scaffold for preventing compression and instability in a segmental bone defect according to one or more embodiments of the present invention taken transverse the bone axis showing the spacial relationship between the struts on the outer shell and grooves in the substantially hollow insert.
Figure 5C:
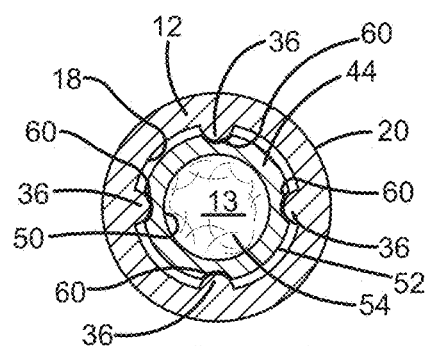
FIG. 5C is a cross sectional view of a polymer scaffold for preventing compression and instability in a segmental bone defect according to one or more embodiments of the present invention taken transverse the bone axis showing the spatial relationship between the struts on the outer shell and grooves in the substantially hollow insert.
Figure 5D:
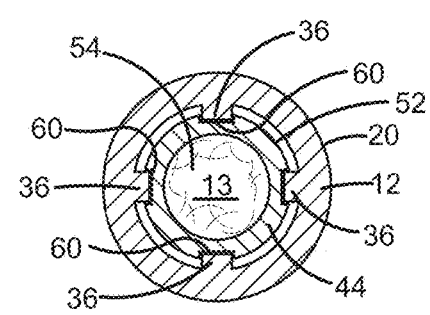
FIG. 5D is a cross sectional view of a polymer scaffold for preventing compression and instability in a segmental bone defect according to one or more embodiments of the present invention taken transverse the bone axis showing the spacial relationship between the struts on the outer shell and grooves in the substantially hollow insert.
Figure 6:
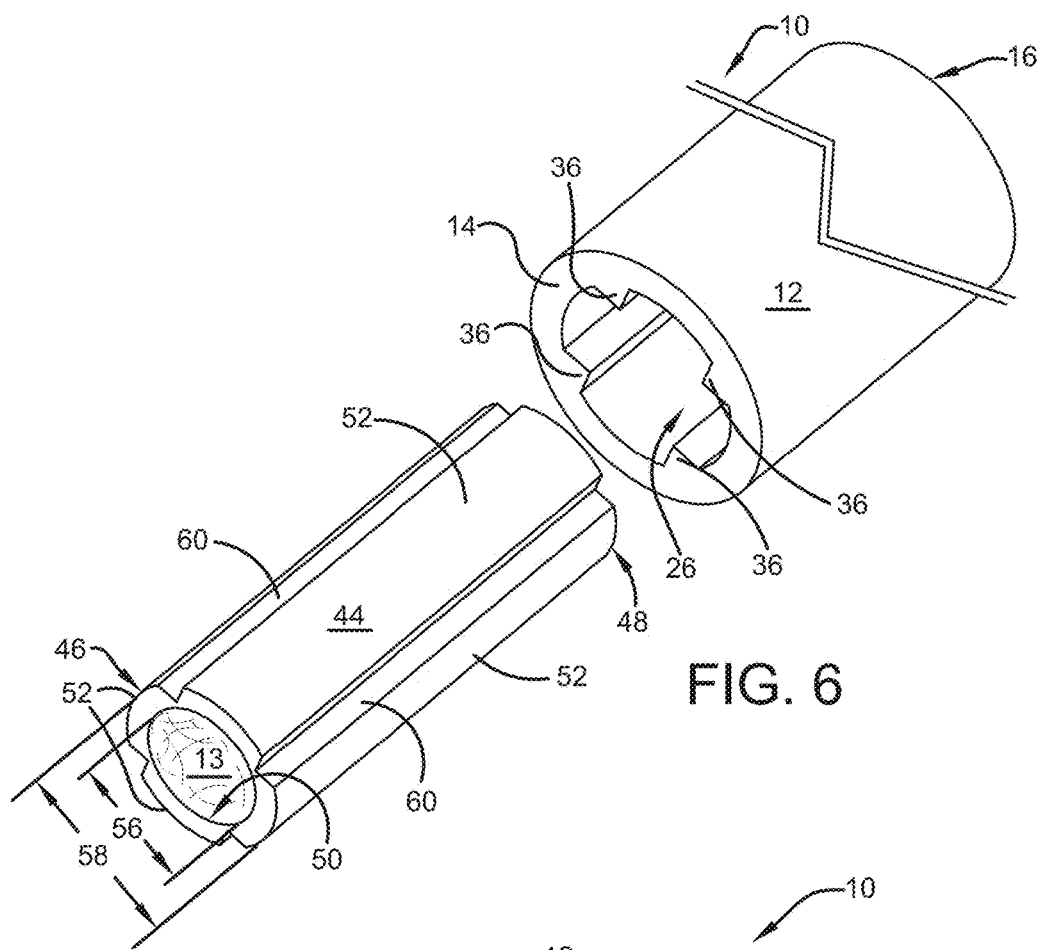
FIG. 6 is an exploded view of a polymer scaffold for preventing compression and instability in a segmental bone defect according to one or more embodiments of the present invention.
Figure 7:
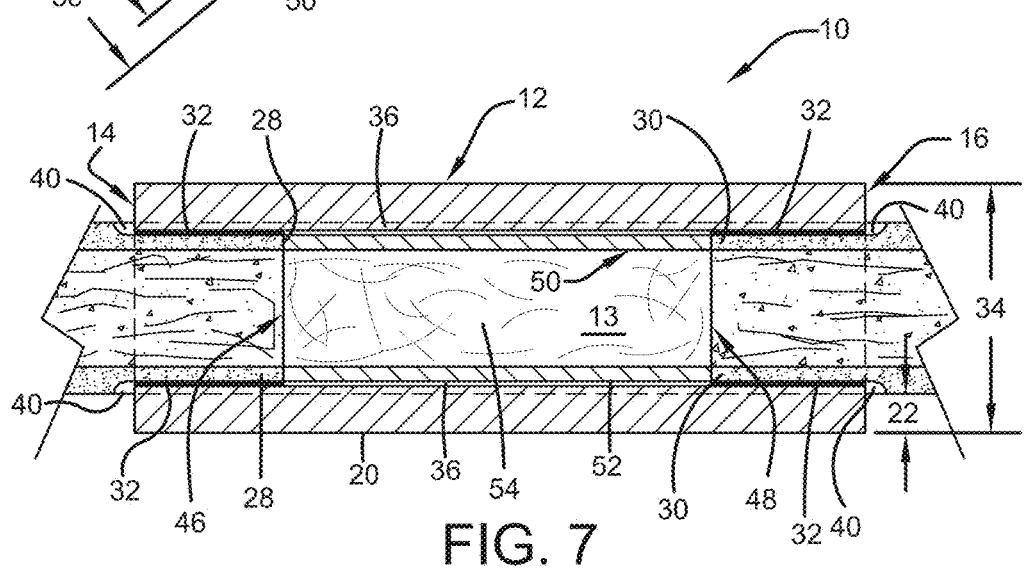
FIG. 7 is a cross sectional view of the polymer scaffold for preventing compression and instability in a segmental bone defect shown in FIG. 5 taken along the bone axis.

The degradation profiles of the polymers used to make the outer shell 12 are likewise important. FIG. 3A-B show the results of in vitro degradation tests done on PHE based PEUs made from diols from 6 to 12 carbons in length. As can be seen from FIG. 3A, all of these PEU polymers are relatively stable and show a relatively small (1%-5%) mass loss through 16 weeks. As can be sees from FIG. 3B, however, PEUs with longer diols exhibited faster degradation (~5%). The in vitro degradation time of the C6-PHE-PEU (Poly(1-PHE-6)) was minimal out to 16 weeks (<1% by mass), whereas the degradation for the C12-PHE-PEU was almost 6 times greater (~6% by mass).

In some embodiments, outer shell 12 may comprise, without limitation, poly(1-PHE-6), poly(1-PHE-8), poly(1-PHE-10), poly(1-PHE-12), poly(1-PHE-14), poly(1-PHE-16), poly(1-PHE-18), poly(1-PHE-20), poly(1-IPHE-6), poly(1-IPHE-8), poly(1-IPHE-10), poly(1-IPHE-12), poly(1-IPHE-14), poly(1-IPHE-16), poly(1-IPHE-18), poly(1-IPHE-20), poly(bis-L-phellylalanine-hexane-1,6-diester-co-tri-O-benzyl-L-tyrosine-1,1,1-trimethyl ethane-triester urea), or combinations and/or copolymers thereof.

In some embodiments, outer shell 12 may be made from a melt extruded polymer including, without limitation, poly (1-PHE-6), poly(1-PHE-8), poly(1-PHE-10), poly(1-PHE-12), poly(1-PHE-14), poly(1-PHE-16), poly(1-PHE-18), poly(1-PHE-20), poly(1-IPHE-6), poly(1-IPHE-8), poly(1-IPHE-10), poly(1-IPHE-12), poly(1-IPHE-14), poly(1-IPHE-16), poly(1-IPHE-18), poly(1-IPHE-20), poly(bis-L-phellylalanine-hexane-1,6-diester-co-tri-O-benzyl-L-tyrosine-1,1,1-trimethyl ethane-triester urea), or combinations and/or copolymers thereof.

In some embodiments, the one or more of the polymers used to form the outer shell 12 may be radiopaque to facilitate post surgical imaging of the constructs using commercial imaging equipment. Any suitable radiopaque polymer known in the art having the required mechanical and degradation properties may be used. In some embodiments, outer shell 12 may include radiopaque versions of degradable poly(urethane) and/or poly(ester urea) polymers. In some embodiments, the outer shell 12 may comprise one or more radiopaque PEU polymers having the formula:

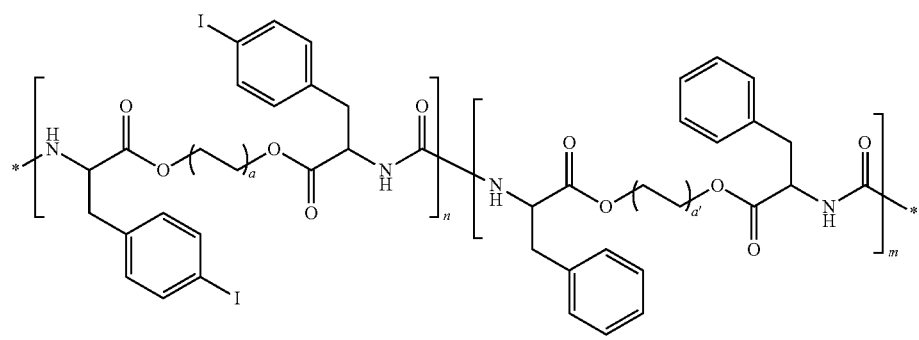

(XVI)

wherein a and a' are each an integer from 2 to 20; n is a mole fraction of iodinated PHE based amino acid segments; and m is a mole fraction of (non-iodinated) PHE based amino acid segments. In some other embodiments,

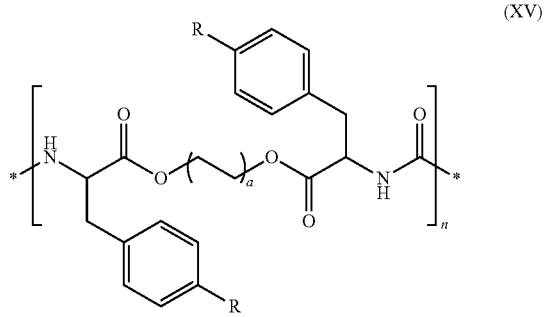

(XV)

wherein R is H and/or a large radiopaque atom such as iodine, boron or combinations thereof, a is an integer from about 1 to about 10, and n is an integer from about 10 to about 1000.

Turning now to the embodiments shown in FIGS. 4A-D, outer shell 12 may have one or more struts 36 running along its inner surface 18 between the first end 14 and second end 16 of the outer shell 12 to provide additional mechanical strength. As can be seen in FIGS. 4A-D, struts 36 may have any cross sectional shape. Suitable cross sectional shapes include, without limitation, triangular, rounded, square, and rectangular. Struts 36 also have a strut height 38, which may be defined as the distance the strut travels from the inner surface 18 into the inner cavity 26 of outer shell 12.

In these embodiments, outer shell 12 is secured to bone ends 28, 30 as set forth above, except that bone grooves 40 may be cut in bone ends 28, 30 to accommodate struts 36. Bone grooves 40 may be made in bone ends 28, 30 in any suitable manner known in the art. In some embodiments, bone grooves 40 may be cut in bone ends 28, 30 using a high speed electric trephine burr or other orthopaedic tool appropriate for shaping bone. This may greatly improve the ability of the outer shell 12 to resist both linear and rotational movement with respect to the bone ends 28, 30, but also may place limitations on the strut height 38, the number of struts 36 and, to some degree, the cross sectional shape of the struts that may be used. As should be apparent, it is important that these bone grooves 40 not adversely affect the mechanical strength and integrity of the bone ends 28, 30. As the height, number, and shape of the struts 36 affect the amount and location of the bone that must be removed from bone ends 28, 30 to accommodate the outer shell 12, care should be taken not to remove bone in an amount or location that adversely affects the mechanical strength and/or integrity of the bone ends 28, 30.

Accordingly, in these embodiments, strut height 38 is preferably substantially less than thickness of the bone at bone ends 28, 30. In some embodiments, strut height 38 may be from about 0.05 mm to about 2.5 mm. In some embodiments, strut height 28 may be from about 0.05 mm to about 2.0 mm. In some embodiments, strut height 38 may be from about 0.05 mm to about 1.5 mm. In some embodiments, outer shell 12 may have from 2 to 8 struts. In some embodiments, outer shell 12 may have from 2 to 6 struts. In some embodiments, outer shell 12 may have from 2 to 5 struts. In some embodiments, outer shell 12 may have 4 struts. In some embodiments, struts 36 are symmetrically oriented around the inner surface 18 of the outer shell 12.

In some embodiments, the struts 36 comprise from about 2% to about 20% of the inner cavity 26 of outer shell 12. In some embodiments, the struts 36 comprise from about 2% to about 15% of the inner cavity 26 of outer shell 12. In some embodiments, the struts 36 comprise from about 2% to about 10% of the inner cavity 26 of outer shell 12. In some embodiments, the struts 36 comprise from about 1% to about 5% of the inner cavity 26 of outer shell 12. In some embodiments, the struts 36 comprise from about 1% to about 3% of the inner cavity 26 of outer shell 12.

Polymer scaffold 10 further comprises a collagen containing material 13, such as decellularized horse tendon, which is placed in the inner cavity 26 of outer shell 12 to facilitate regrowth of bone in the defect area. Collagen containing material 13 should be non-toxic and biocompatible and may contain structural proteins such as: elastin, laminin; functional proteins such as growth factors and cytokines, polysaccharides or mineral phases. A collagen shell mimicking the structure and composition of the periosteum will accelerate bone formation and allow the bridging of a segmental bone defect. In some embodiments, collagen containing material 13 may be decellularized horse tendon, which is commercially available from OPOCRIN SPA, among other others. While not wishing to be bound by theory, it is believed that the collagen containing material assists in bone regrowth by natural feed stock for hone regrowth.

A significant challenge in this process is limiting the compression of the bone on the collagen containing material 13 within scaffold 10 during patient movement following surgery. Accordingly, in some embodiments, polymer scaffold 10 may include a substantially hollow insert 44 sized to fit within said segmental bone defect and within said outer shell 12. Polymer insert 44 is substantially hollow and has a first (proximal) end 46, a second (distal) end 48, an inner surface 50, an outer surface 52, a central cavity 54, an inner diameter 56 and an outer diameter 58 that is less than the inner diameter 24 of outer shell 12. Polymer insert 44 is sized to fit within outer shell 12 and between first bone end 28 and second bone end 30 (See FIGS. 5A-D, 6 and 7) in order to prevent compression of the hone on the collagen containing material 13 within scaffold 10 during patient movement following surgery and may be filled with collagen containing material 13. In these embodiments, the central cavity 54 of polymer insert 44 (rather than the inner cavity 26 of outer shell 12) may be filled with collagen containing material 13 to facilitate regrowth of bone in the defect area.

Polymer insert 44 may be made from any of the polymers discussed above with respect to outer shell 12, including, without limitation, poly(1-PHE-6), poly(1-PHE-8), poly(1-PHE-10), poly(1-PHE-12), poly(1-PHE-14), poly(1-PHE-16), poly(1-PHE-18), poly(1-PHE-20), poly(1-IPHE-6), poly(1-IPHE-8), poly(1-IPHE-10), poly(1-IPHE-12), poly(1-IPHE-14), poly(1-IPHE-16), poly(1-IPHE-18), poly(1-IPHE-20), poly(bis-L-phellylalanine-hexane-1,6-diester-co-tri-O-benzyl-L-tyrosine-1,1,1-trimethyl ethane-triester urea), or combinations and/or copolymers thereof. In some embodiments, insert 44 may be constructed of the same material as outer shell 12. In some other embodiments, insert 44 may be constructed of a different material than that of outer shell 12.

In some embodiments, the substantially hollow insert 44 may be used together with outer shell 12 as shown in FIGS. 5B-D, 6 and 7. In these embodiments, outer shell 12 has one or more struts 36 and insert 44 includes one or more corresponding grooves running along the outer surface 52 of the substantially hollow insert 44, sized to receive one or more struts 36 running along the inner surface 18 of said outer shell 12.

Outer shell 12 and insert 44 may be fabricated using any conventional method, including, but not limited to melt extrusion, injection molding, 3D printing, or compression molding. In some embodiments, the selected polymer is ground to a powder, dried, and melt extruded through an appropriate dye to form outer shell 12 or insert 44. In some embodiments. Outer shell 12 and insert 44 may be shaped or modified interoperatively using a diamond saw or similar cutting instrument. In some embodiments, the outer shell may be extruded as set forth in Example 2.

In another aspect, the present invention is directed to a method of treating a segmental defect in a long bone using the polymer scaffolds described above. In these embodiments, the patient is first placed under anesthesia, prepared for surgery and draped in typical sterile fashion. Next, an incision extending from above the defect to below the defect is be made through the skin and extending through the subcutaneous tissue and fascia to expose the periosteum covering the defect. A second incision is then made in the periosteum to expose the segmental bone defect. If the bone at the segmental bone defect is not continuous, the bone ends above and below the segmental bone defect are located and identified and any crushed bone or fragments of bone removed. In some embodiments, the damaged bone ends above and below the defect are removed to create bone ends to which the polymer scaffold may be attached. If the bone at the segmental bone defect is continuous, the bone may be cut and/or the damaged section of bone removed to provide bone ends above and below the defect to which the polymer scaffold may be attached.

A polymer scaffold as described above is then selected and, if necessary, modified to fit over the defect. In some embodiments, the polymer scaffold is prepared prior to surgery to fit the particular bone and none defect. In some embodiments, the surgeons may modify the polymer scaffold in the operating room to ensure a proper fit. In some embodiments, a collagen containing material, such as decellularized horse tendon, is placed into the central cavity of the scaffold. The polymer scaffold is then slipped over the ends of the bone and secured in place by means of a non-toxic adhesive, material; said outer shell having a first end sized to fit over said first bone end, a second end sized to fit over said second bone end, an inner cavity, and a length that is greater than the length of said segmental bone defect; placing the collagen containing material in the inner cavity of said outer shell; sliding the first end of said polymer shell over said first bone end and securing it in place with a non-toxic adhesive; sliding the second end of said polymer scaffold over said second bone end and securing it in place with a non-toxic adhesive; surgically closing the wound exposing said segmental bone defect.

Depending upon the nature and size of the defect, a natural, grafted, or artificial periosteum may be secured circumferentially around the repair site. In some embodiments, a natural, grafted, or artificial periosteum may be secured circumferentially around the repair sight with a suture. The muscular fascia and subcutaneous tissues are then approximated in separate layers circumferentially as far as possible around the repair site in running fashion using an absorbable suture. Finally, the skin is approximated with an absorbable suture and Dermabond applied on top of the incision. A heavy support wrap cast and splint may then applied.

In some embodiments, a polymer insert containing the collagen containing material and sized to fit inside said outer shell and between said first bone end and said second bone end is inserted into the central cavity of the outer shell of the scaffold, rather than the collagen containing material as described above.

The polymer scaffold of one or more embodiments of the present invention has been shown in animal tests to facilitate the healing of a segmental bone defects. In these experiments, a tube shaped outer shell according to one or more embodiments of the present invention was made from degradable PEU polymer tube, filled with a collagen containing material (decellularized horse tendon), and surgically placed across a segment defect surgically generated in the tibia of eight sheep. The polymer scaffold was glued in place and stabilized with a cast and partial load bearing splint, and bone regrowth evaluated by x-ray, ultrasound, and CT at regular intervals. It was found that over a period of 4 weeks to 4 months that new bone filled the gap (defect) and resulted in a stable repair that appears to remodel over time. (See FIGS. 8A-D and 9, and Example 3, below)

In light of the foregoing, it should be appreciated that the present invention significantly advances the art by providing a novel polymer scaffold design and method for treating segmental long bone defects that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Synthesis of
bis-L-phenylalanine-1,6-hexanediol-diester PEU Polymer 1,6-hexanediol (20.00 g, 1.0 equiv., 0.17 mol), L-phenylalanine (64.32 g, 2.3 equiv., 0.39 mol), p-toluene sulfonic acid monohydrate (77.29 g, 2.4 equiv., 0.41 mol) and toluene (500 mL) were mixed in a 1 L one-neck round-bottomed flask using a magnetic stir bar with a dean stark trap. The system was refluxed at 110° C. for 21 h. The crude product was vacuum filtered overnight to remove toluene, decolorized by activated carbon black (4.00 g) and recrystallized from boiling water 4 times to yield 105.50 g (yield 82.4%). $^1$H-NMR (500 MHz, DMSO-$d_6$): 1.06 (m, 4H), 1.38 (m, 4H), 2.27 (s, 6H), 2.48 (m, DMSO), 2.97-3.15 (m, 4H), 3.29 (s, $H_2O$), 3.98-4.03 (m, 4H), 4.25-4.28 (m, 2H), 7.09-7.11 (d, 4H), 7.20-7.30 (m, 10H), 7.41-7.49 (d, 4H), 8.36 (s, 6H). $^{13}$C-NMR (500 MHz, DMSO-$d_6$): 20.84, 24.72, 27.65, 36.22, 38.67-39.78 (DMSO-$d_6$), 53.36, 65.48, 125.56, 127.26, 128.24, 128.58, 129.34, 134.73, 138.14, 145.03, 169.08.

Di-p-toluene sulfonic acid salt of bis-L-phenylalanine-1,6-hexanediol-diester (1-PHE-6 monomer) (30.00 g, 1.0 equiv., 0.04 mol), sodium carbonate (8.83 g, 2.1 equiv., 0.083 mol) and 400 mL distilled water were added to a 3 L 3-neck round bottom flask. The contents were mechanically stirred at 35° C. until the mixture was dissolved. The 35° C. water bath was then replaced with an ice bath. When the reaction temperature reached 0° C., additional sodium carbonate (4.42 g, 1.05 equiv., 0.042 mol) was dissolved in 150 mL distilled water and added to the flask. Triphosgene (4.21 g, 0.35 equiv., 0.014 mol, 98%), dissolved in distilled chloroform (100 mL), was added to the flask quickly. After 30 minutes, additional triphosgene (1.00 g, 0.08 equiv., 0.003 mol, 98%), dissolved in distilled chloroform (30 mL), was added to the flask dropwise for 2 h. The crude product was transferred to a separatory funnel and precipitated into boiling water dropwise to obtain bis-L-phenylalanine-1,6-hexanediol-diester PEU (poly(1-PHE-6)) PEU polymer) 15.99 g (yield 92.0%). $^1$H-NMR (500 MHz, DMSO-$d_6$): 1.15 (m, 4H) 1.43 (m, 4H) 2.49 (DMSO) 2.85-2.94 (m, 4H) 3.29 (s, $H_2O$), 3.94 (m, 4H) 4.35-4.39 (m, 2H) 6.47-6.48 (m, 2H) 7.13-7.26 (m, 10H). $^{13}$C-NMR (500 MHz, DMSO-$d_6$): 25.32, 28.35, 38.15, 39.52-40.53 (DMSO), 54.50, 64.72, 126.97, 128.65, 129.59, 137.33, 157.09, 172.70.

Example 2

Fabrication of PEU Polymer Scaffold

Before extrusion, the PUE polymer solid of Example 1 was be ground to fine powder using a high speed grinder equipped with rotating blades. The prepared powder was dried overnight in a vacuum oven at a temperature of 40° C. The dried powder was flood fed into a Killion one inch (25.4 mm) single-screw extruder with L/D ratio of 24 equipped with an annular die. The temperature of the barrel near the feeding zone will be set at 150° C. while in other zones of the extruder barrel will be set at 160° C. The temperature of the transition piece connecting the barrel and the annular die was set at 100° C. The temperature of the die was set about 95° C. The outer and inner diameter of the die was 36 mm, and 25 mm, respectively, and its land length was 15.2 mm. The screw rotation speed of the extruder was set at 20 rpm depending on the received material. This variation in the screw rotation speed was necessary to obtain well-shaped tubes satisfying the requirements in the absence of tube calibration equipment. The scaffold tube was vertically extruded into atmosphere, cut and cooled to room temperature.

Example 3

Bone Regeneration of a Tibial Segmental Defect in Sheep

Polymer scaffolds formed as set forth in Example 2 above, were implanted in eight mature Suffolk sheep after creation of a tibial critical sized defect that preserved the mid-diaphyseal periosteum and bone regrowth monitored over a period of six months.

Surgical Procedure

After induction of general anesthesia, the sheep's right hindlimb was shaved, then prepped and draped in typical sterile fashion. The medial midpoint of the tibia was identified and locally blocked with bupivacaine (1-2 mg/kg). A longitudinal incision approximately 12 cm in length was made from the skin extending through the underlying subcutaneous tissue and fascia to adequately expose the tibial periosteum. A scalpel and/or bovie electrocautery was used to create a similar longitudinal incision approximately 10 cm long in the periosteum to expose the tibia. Circumferential exposure was undertaken, stripping periosteum and soft tissues from the tibia mimicking a human traumatic situation. Using a surgical marker, the bone was marked directly with lines delineating the proposed defect, and a single longitudinal line extending proximal and distal from the defect site to provide maintenance of proper axial alignment after defect repair using the PEU Shell. A 30 mm segment of bone (midshaft) was excised from the tibia via parallel controlled osteotomies made with a Stryker reciprocating saw.

Figure 9A:
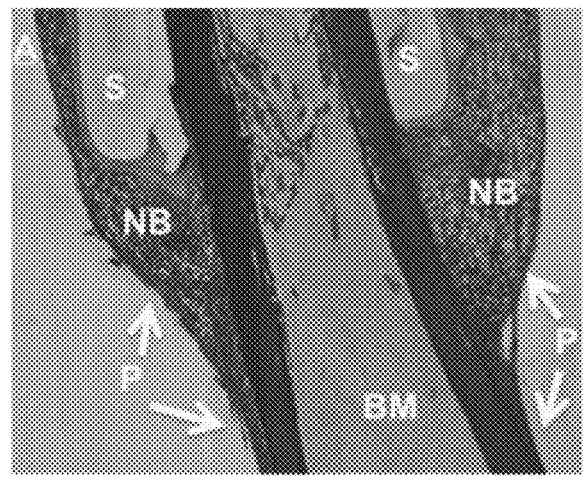
FIGS. 9A-E are images taken from slides of a Masson's Trichrome staining showing a saggital section of the sheep regenerating long-bone defect after 4 weeks post implant.
Figure 9B:
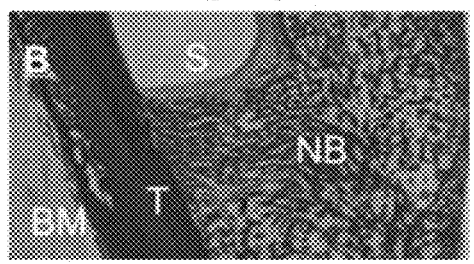
Figure 9C:
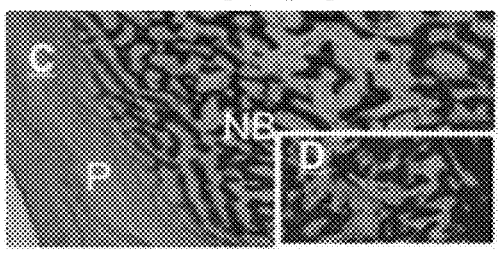
Figure 9D:
Figure 9E:

The muscular fascia and subcutaneous tissues were approximated in separate layers circumferentially as far as possible around the repair site in running fashion using 2-0 or 3-0 PDS or Vicryl absorbable suture. Finally, the skin was approximated with a subcuticular 4-0 Monocryl absorbable suture and Dermabond was applied on top of the incision. A heavy support wrap cast and splint (modified Schroeder-Thomas) were applied intraoperatively prior to recovering the animal Bone Regrowth It is known that ossification of the soft callus transforms it into a harder bony callus that bridges fracture defect fragments with woven bone. The histological evidence clearly demonstrates that after 4 weeks, healing at the defect site is already at the stage of the hard, bony callus (FIGS. 9A-E). Using Masson's trichrome stain, spicules of woven bone can be seen attempting to bridge the entire thickness of new tissue growth from shell surface to the periosteum (FIG. 9A). The process of endochondral ossification can be also appreciated with Masson's trichrome staining, where distinctly blue-staining (dense collagen and bone) tissue can be seen within the center of the bony callus as well as at the immediate sub-periosteal surface (FIGS. 9B-D). Finally, areas of fusion were confirmed histologically at the interface of native tibia, PEU Shell edge and novel bone (FIG. 9E). It is believed that had the internal immobilization of bony fragments by the PEU outer shell been insufficient, fibrous nonunion would have occurred.

Figure 10:
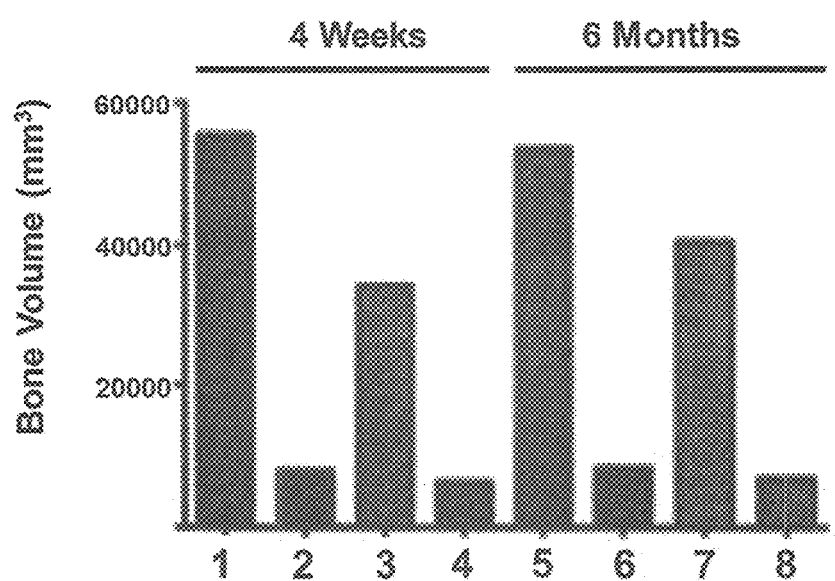
FIG. 10 is a graphical representation of new bone quantification after 4 weeks and 6 months implantation. The amount of bone generated at the 200 HU threshold columns 1, 2, 5, and 6), which includes both the trabecular and cortical bone, and 500 HU threshold (columns 3, 4, 7, and 8) for cortical bone only. The first bar (Column 1) in each series represents the experimental average value and the second bar (Column 5) shows the baseline control value from the tibia.

In addition, bone volume was calculated at 4 weeks (FIG. 8C) and at 6 months post operatively (FIG. 8D), and were compared to the baseline tibial pre-defect value. Radiographically, a shocking 9 centimeters longitudinal length and several centimeter thick envelope of novel bone was appreciated already at 4 weeks postoperatively (FIG. 8C) covering the PEU Shell (FIG. 8B) implanted to bridge the tibial defect (FIG. 10A). To further substantiate both the quantity and quality of the new bone formed, total new bone volumes were quantified. DICOM files from the experimental animal CTs were analyzed using a Siemens INVEON software system. Tissues of differing structure/density can be differentiated by Hounsfield Units (HU). Our thresholds were chosen based on literature stating that trabecular (woven) bone typically displays HU as low as 100 and as high as 450, while cortical bone has HU values >50. Thresholds of 200 HU (representing the total new bone formed, trabecular+cortical) and 500 HU (cortical alone) were thus acceptable conservative metrics to stratify the novel bone.

Figure 8A:
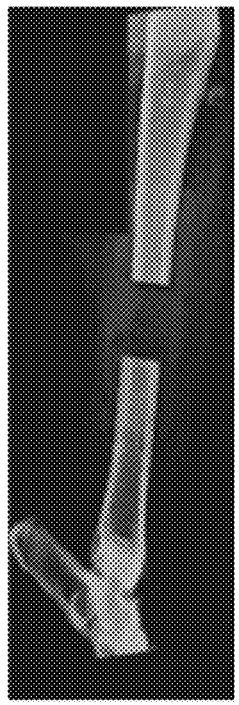
FIG. 8A is an x-ray image of showing the posterolateral view of a tibia with a surgically created segmental defect.
Figure 8B:
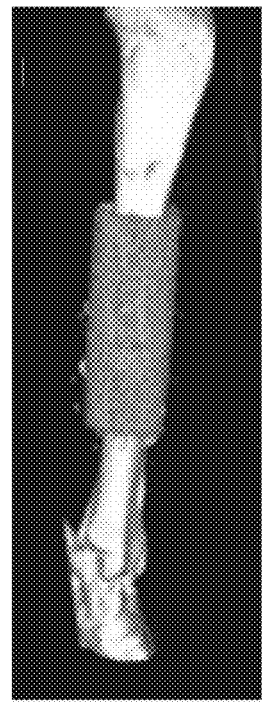
FIG. 8B is a posterolateral view of the tibia shown in FIG. 8A after installation of a polymer scaffold according to embodiments of the present invention.
Figure 8C:
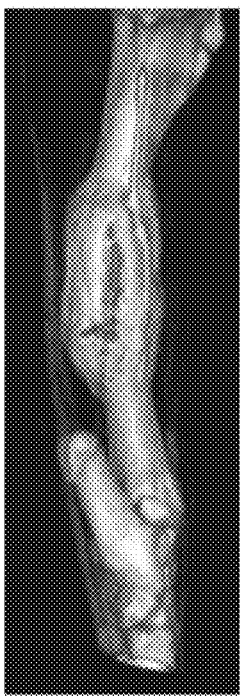
FIG. 8C is a posterolateral view of the tibia shown in FIG. 8A taken at 4 weeks postoperatively.
Figure 8D:
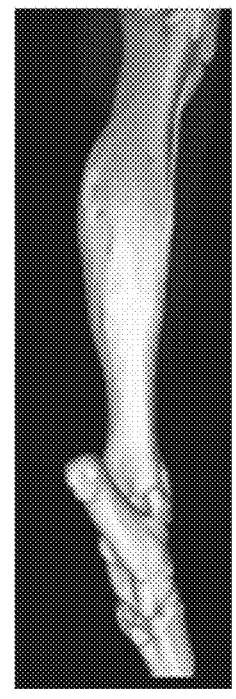
FIG. 8D is a posterolateral view of the tibia shown in FIG. 8A taken at 6 months postoperatively. Note full circumferential bone regeneration with no remaining defect.

At 4 weeks, the average total new bone volume (200 HU) was 55576.9 mm$^3$ and new cortical bone (500 HU) was 34123.1 mm$^3$ compared to baseline tibial values of 7905.8 mm$^3$ and 6358.4 mm$^3$ respectively—a difference of over 704% for total bone and 540% for cortical. The same phenomenon held true at 6 months, with experimental total new bone and cortical volumes of 53580.3 and 40509.2 mm$^3$—a difference of nearly 650% and 585% respectively. (See FIG. 10) Fracture/defect healing was completed during the remodeling stage, during which the original shape, structure, and mechanical strength is restored to a healing bone. This process typically occurs slowly over months to years and is facilitated by mechanical stresses placed on the bone, with adequate strength usually achieved in 3 to 6 months. At 4 weeks postoperatively, the new cortical bone volume accounts for 61.4% of the total new bone volume, but increases to 75.6% of the total at 6 months while the total new bone volume remained almost identical (55576.9 versus 53580.3 mm$^3$, a difference of less than 4%). Comparative views of 3D reconstructive CT renderings of 4 weeks versus 6 months give visual evidence of this beautiful remodeling process, as the bulky circumferential bony callus at 4 weeks is converted to a smooth, seamless transition from native tibia to novel bone (FIG. 8D).

Taken together with the histological findings, several key facts about the success of our defect repair and regeneration may be concluded: the PEU outer shell has an osteoconductive effect in the setting of bony defect repair; the PEU outer shell provided more than sufficient internal biomechanical stability to allow early cast support removal while regeneration/remodeling occur; the novel bone formed is higher in volume and maturity than one would have been expect within the specified timeframe, and the process by which the bone is formed is perfectly in line with what one would expect for normal bone healing and remodeling.

Functional Recovery

Over a period of four weeks upon removal of the splint, the treated animals exhibited increased frequency of standing, decreased tachypnea and full weight bearing in 6 weeks and had no observable gait deficits by week 8 postoperatively. By this time, the implanted shell construct and surrounding new bone formation was sturdy enough to withstand the forces of walking, trotting, balancing on the hindlimbs and jumping. After the twelfth week it became virtually impossible for trained personnel to distinguish which limb was affected. The sheep recovered full ambulatory capability with no gait deficits or pain—unexpected and remarkable feat given the invasive nature/severity of the operative procedure.

What is claimed is:

1. A polymer scaffold for preventing compression and instability in a segmental bone defect comprising:
    a tubular outer shell sized to fit over a segmental defect in a bone; said tubular outer shell having a first end, a second end; an inner surface, an outer surface, one or more struts running along the inner surface of said tubular outer shell between the first end and second end of said outer shell, a thickness and an internal diameter; said inner surface defining an inner cavity; and
    a collagen containing material located within the inner cavity of said tubular outer shell.

2. The polymer scaffold of claim 1, further comprising an insert sized to fit within said segmental bone defect and within said tubular outer shell; said insert having a first end, a second end, an inner surface, an outer surface, and a central cavity; wherein said collagen containing material is located within the central cavity of said insert.

3. The polymer scaffold of claim 2, wherein:
said insert has one or more grooves running along the outer surface of said surface substantially hollow insert; said one or more grooves sized to receive the one or more struts running along the inner surface of said tubular outer shell.

4. The polymer scaffold of claim 3, wherein the grooves running along the outer surface of said insert have a triangular, rectangular, square or rounded cross sectional shape.

5. The polymer scaffold of claim 2, wherein said insert comprises a degradable poly(urethane), poly(ester urea), or poly(ester) polymer.

6. The polymer scaffold of claim 5, wherein said insert comprises a polymer selected from the group consisting of poly(1-PHE-6), poly(1-PHE-8), poly(1-PHE-10), poly(1-PHE-12), poly(1-PHE-14), poly(1-PHE-16), poly(1-PHE-18), poly(1-PHE-20), poly(1-IPHE-6), poly(1-IPHE-8), poly(1-IPHE-10), poly(1-IPHE-12), poly(1-IPHE-14), poly(1-IPHE-16), poly(1-IPHE-18), poly(1-IPHE-20), poly(bis-L-phellylalanine-hexane-1,6-diester-co-tri-O-benzyl-L-tyrosine-1,1,1-trimethyl ethane-triester urea), and combinations or copolymers thereof.

7. The polymer scaffold of claim 2, wherein at least one of said tubular outer shell and insert are radiopaque.

8. The polymer scaffold of claim 1, wherein said tubular outer shell comprises a degradable poly(urethane), poly(ester urea), poly(carbonate) or poly(ester) polymer.

9. The polymer scaffold of claim 1, wherein said tubular outer shell comprises a polymer selected from the group consisting of poly(1-PHE-6), poly(1-PHE-8), poly(1-PHE-10), poly(1-PHE-12), poly(1-PHE-14), poly(1-PHE-16), poly(1-PHE-18), poly(1-PHE-20), poly(1-IPHE-6), poly(1-IPHE-8), poly(1-IPHE-10), poly(1-IPHE-12), poly(1-IPHE-14), poly(1-IPHE-16), poly(1-IPHE-18), poly(1-IPHE-20), poly(bis-L-phellylalanine-hexane-1,6-diester-co-tri-O-benzyl-L-tyrosine-1,1,1-trimethyl ethane-triester urea), and combinations or copolymers thereof.

10. The polymer scaffold of claim 1, wherein said tubular outer shell comprises a radiopaque polymer.

11. The polymer scaffold of claim 1, wherein the internal diameter of said outer shell is from about 1 cm to about 5 cm and the thickness of said outer shell is from about 2 mm to about 6 cm.

12. The polymer scaffold of claim 1, wherein the inner surface of said tubular outer shell has from about 2 to about 5 struts.

13. The polymer scaffold of claim 12, wherein said struts are symmetrically oriented around the inner surface of said outer shell.

14. The polymer scaffold of claim 1, wherein the struts comprise from about 2% to about 20% of the internal diameter of said outer shell.

15. The polymer scaffold of claim 1, wherein said struts have a rounded cross sectional shape.

16. The polymer scaffold of claim 1, wherein said collagen containing material comprises at least one of collagen, decellularized tissue, and decellularized horse tendon.

17. A method of treating a segmental bone defect using a polymer scaffold comprising:
A. applying anesthesia to the patient;
B. surgically exposing the segmental bone defect, if not already exposed;
C. determining whether the segmental bone defect is continuous or not continuous;
D. if the bone at the segmental bone defect is not continuous, identifying a first bone end and a second bone end;
E. if the bone at the segmental bone defect is continuous, cutting through the bone at the segmental bone defect to create said first bone end and said second bone end;
F. preparing a polymer scaffold comprising a tubular outer shell and; said tubular outer shell having a first end sized to fit over said first bone end, a second end sized to fit over said second bone end, an inner cavity, and a length that is greater than the length of said segmental bone defect and a polymer insert sized to fit inside said tubular outer shell and between said first bone end and said second bone end, said polymer insert having a first end, a second end, an inner surface, an outer surface, and a central cavity the inner cavity of said tubular outer shell;
G. placing a collagen containing material in the central cavity of said polymer insert and inserting said substantially hollow polymer insert into the inner cavity of said solid tubular outer shell;
H. sliding the first end of said solid tubular shell over said first bone end and securing it in place with a non-toxic adhesive;
I. sliding the second end of said solid tubular shell over said second bone end and securing it in place with a non-toxic adhesive;
J. surgically closing the wound exposing said segmental bone defect.

18. The method of claim 17 wherein:
said tubular outer shell has one or more struts running along the inner surface of said outer tubular shell between the first end and second end of said tubular outer shell; and
said polymer insert has one or more grooves running along the outer surface of said polymer insert; said one or more grooves sized to receive the one or more struts running along the inner surface of said tubular outer shell.

19. The method of claim 18 wherein at least one of the step of sliding the first end of said tubular shell over said first bone end (Step H) or the step of sliding the second end of said solid tubular shell over said second bone end (Step I) further comprises forming one or more grooves in an outer surface of said first bone end or said second bone end sized to receive one or more of said one or more struts running along the inner surface of said outer shell between the first end and second end of said outer shell.

20. The method of claim 17 wherein the step of preparing a polymer scaffold further comprises making said tubular outer shell by melt extrusion of a polymer selected from the group consisting of poly(1-PHE-6), poly(1-PHE-8), poly(1-PHE-10), poly(1-PHE-12), poly(1-PHE-14), poly(1-PHE-16), poly(1-PHE-18), poly(1-PHE-20), poly(1-IPHE-6), poly(1-IPHE-8), poly(1-IPHE-10), poly(1-IPHE-12), poly(1-IPHE-14), poly(1-IPHE-16), poly(1-IPHE-18), poly(1-IPHE-20), poly(bis-L-phellylalanine-hexane-1,6-diester-co-tri-O-benzyl-L-tyrosine-1,1,1-trimethyl ethane-triester urea), and combinations or copolymers thereof, through a dye.

* * * * *

UNITED STATES PATENT AND TRADEMARK OFFICE
CERTIFICATE OF CORRECTION

PATENT NO. : 10,206,781 B2
APPLICATION NO. : 15/310981
DATED : February 19, 2019
INVENTOR(S) : Matthew Becker et al.

Page 1 of 1

It is certified that error appears in the above-identified patent and that said Letters Patent is hereby corrected as shown below:

In the Specification

Column 1, Line 20, delete "W911NF-09-1-004" and insert --W911NF-09-1-0044--

Column 1, Lines 20-21, delete "Defense Advanced Research Projects Agency (DARPA)" and insert --DARPA U.S. Army Research Office--

Signed and Sealed this
Twenty-eighth Day of May, 2019

Andrei Iancu
*Director of the United States Patent and Trademark Office*